US012708370B2

(12) United States Patent
Korkuch

(10) Patent No.: US 12,708,370 B2
(45) Date of Patent: Aug. 18, 2026

(54) SYSTEMS AND METHODS FOR SELECTIVE OCCLUSION OF THE PERIPHERAL VENOUS VASCULATURE TO UNLOAD THE HEART

(71) Applicant: ABIOMED, INC., Danvers, MA (US)

(72) Inventor: Christopher Korkuch, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 505 days.

(21) Appl. No.: 18/329,188

(22) Filed: Jun. 5, 2023

(65) Prior Publication Data

US 2023/0389935 A1 Dec. 7, 2023

Related U.S. Application Data

(60) Provisional application No. 63/365,941, filed on Jun. 6, 2022.

(51) Int. Cl.
*A61B 17/12* (2006.01)
*A61M 25/10* (2013.01)
*A61M 60/13* (2021.01)
*A61M 60/531* (2021.01)

(52) U.S. Cl.
CPC ....... *A61B 17/12136* (2013.01); *A61M 25/10* (2013.01); *A61M 60/13* (2021.01); *A61M 2025/1052* (2013.01); *A61M 60/531* (2021.01)

(58) Field of Classification Search
CPC . A61B 17/12136; A61M 60/13; A61M 25/10; A61M 60/531; A61M 2025/1052
See application file for complete search history.

(56) References Cited

U.S. PATENT DOCUMENTS

| | | | |
|---|---|---|---|
| 4,546,759 | A | 10/1985 | Solar |
| 4,576,181 | A | 3/1986 | Wallace et al. |
| 4,610,256 | A | 9/1986 | Wallace |

(Continued)

FOREIGN PATENT DOCUMENTS

| | | | |
|---|---|---|---|
| CN | 1819855 | A | 8/2006 |
| EP | 2353501 | A1 | 8/2011 |

(Continued)

OTHER PUBLICATIONS

International Search Report & Written Opinion dated Aug. 23, 2023 in Int'l PCT Patent Appl. Serial No. PCT/US2023/024440 (0510).

(Continued)

*Primary Examiner* — Lindsey G Wehrheim
(74) *Attorney, Agent, or Firm* — Greenberg Traurig, LLP; Christopher C. Bolten; Albert K. Heng

(57) ABSTRACT

Systems and methods for intermittently occluding a patient's venous vasculature to unload the heart while increasing cardiac output and improving perfusion to the patient's heart is provided. The system may include first and second balloon catheters that may be selectively actuated to intermittently occlude first and second veins for increasing venous vascular resistance in the patient's lower and upper extremities, respectively, to thereby selectively reduce arterial blood flow to the lower and upper extremities, while maintaining arterial vascular resistance of the patient's heart and central organs and increasing perfusion to the patient's heart and central organs.

28 Claims, 22 Drawing Sheets

(56) References Cited

U.S. PATENT DOCUMENTS

| | | | |
|---|---|---|---|
| 4,846,787 | A | 7/1989 | Aall-Flood et al. |
| 4,949,723 | A | 8/1990 | Wallace et al. |
| 5,021,046 | A | 6/1991 | Wallace |
| 5,097,840 | A | 3/1992 | Wallace et al. |
| 5,330,451 | A | 7/1994 | Gabbay |
| 5,458,574 | A | 10/1995 | Machold et al. |
| 6,146,354 | A | 11/2000 | Beil |
| 6,485,500 | B1 | 11/2002 | Kokish et al. |
| 6,726,651 | B1 | 4/2004 | Robinson et al. |
| 6,790,043 | B2 | 9/2004 | Aboud |
| 6,843,779 | B1 | 1/2005 | Andrysiak et al. |
| 7,476,200 | B2 | 1/2009 | Tal |
| 7,896,840 | B2 | 3/2011 | Spencer et al. |
| 7,909,794 | B2 | 3/2011 | Briscoe et al. |
| 7,909,844 | B2 | 3/2011 | Alkhatib et al. |
| 7,914,643 | B2 | 3/2011 | Simpson |
| 7,951,259 | B2 | 5/2011 | Duchamp et al. |
| 7,959,667 | B2 | 6/2011 | Ta et al. |
| 7,967,781 | B2 | 6/2011 | Simpson et al. |
| 7,972,299 | B2 | 7/2011 | Carter et al. |
| 8,449,565 | B2 | 5/2013 | Duhay |
| 8,646,325 | B2 | 2/2014 | Hoem et al. |
| 8,679,052 | B2 | 3/2014 | Bellantone |
| 8,876,850 | B1 | 11/2014 | Vollmers et al. |
| 8,968,239 | B2 | 3/2015 | Herrera |
| 9,393,384 | B1 | 7/2016 | Kapur et al. |
| 9,878,080 | B2 | 1/2018 | Kaiser et al. |
| 9,901,722 | B2 | 2/2018 | Nitzan et al. |
| 10,279,152 | B2 | 5/2019 | Kapur et al. |
| 10,639,460 | B2 | 5/2020 | Nitzan et al. |
| 10,653,871 | B2 | 5/2020 | Nitzan et al. |
| 10,758,715 | B2 | 9/2020 | Kapur et al. |
| 10,842,974 | B2 | 11/2020 | Kapur et al. |
| 10,842,975 | B2 | 11/2020 | Kapur et al. |
| 10,926,069 | B2 | 2/2021 | Nitzan et al. |
| 11,612,725 | B2 | 3/2023 | Kapur et al. |
| 11,872,361 | B2 | 1/2024 | Kapur et al. |
| 12,357,799 | B2 | 7/2025 | Kapur et al. |
| 12,402,884 | B2 | 9/2025 | Kapur et al. |
| 2003/0186203 | A1 | 10/2003 | Aboud |
| 2004/0022640 | A1 | 2/2004 | Siess et al. |
| 2004/0064090 | A1 | 4/2004 | Keren et al. |
| 2004/0167376 | A1 | 8/2004 | Peters et al. |
| 2005/0015048 | A1 | 1/2005 | Chiu et al. |
| 2006/0064059 | A1 | 3/2006 | Gelfand et al. |
| 2006/0206029 | A1 | 9/2006 | Yair |
| 2008/0294070 | A1 | 11/2008 | Kinori |
| 2009/0131785 | A1 | 5/2009 | Lee et al. |
| 2010/0318114 | A1 | 12/2010 | Pranevicius et al. |
| 2010/0331876 | A1 | 12/2010 | Cedeno |
| 2011/0202084 | A1 | 8/2011 | Hoem et al. |
| 2011/0282274 | A1 | 11/2011 | Fulton, III |
| 2011/0295177 | A1 | 12/2011 | Mohl |
| 2011/0295302 | A1 | 12/2011 | Mohl |
| 2012/0029466 | A1 | 2/2012 | Callaghan et al. |
| 2013/0023909 | A1 | 1/2013 | Duhay |
| 2015/0201944 | A1 | 7/2015 | Starnes |
| 2015/0223707 | A1 | 8/2015 | Ludoph |
| 2017/0049946 | A1 | 2/2017 | Kapur et al. |
| 2018/0000488 | A1 | 1/2018 | Hu et al. |
| 2018/0243541 | A1 | 8/2018 | Kapur et al. |
| 2019/0070348 | A1 | 3/2019 | Frost |
| 2019/0126014 | A1 | 5/2019 | Kapur et al. |
| 2019/0255302 | A1 | 8/2019 | Kapur et al. |
| 2020/0038566 | A1 | 2/2020 | Johnson et al. |
| 2021/0077792 | A1 | 3/2021 | Kapur et al. |
| 2021/0085525 | A1 | 3/2021 | Palushi et al. |
| 2021/0177425 | A1 | 6/2021 | Kapur et al. |
| 2022/0104828 | A1 | 4/2022 | Keating et al. |
| 2022/0401718 | A1 | 12/2022 | Kapur et al. |

FOREIGN PATENT DOCUMENTS

| | | | | | |
|---|---|---|---|---|---|
| EP | 2353503 | A1 | | 8/2011 | |
| WO | WO-9300037 | A1 | | 1/1993 | |
| WO | WO-9841167 | A1 | * | 9/1998 | .............. A61F 2/07 |
| WO | WO-2004073796 | A2 | | 9/2004 | |
| WO | WO-2013061281 | A1 | | 5/2013 | |
| WO | WO-2015009028 | A1 | | 1/2015 | |
| WO | WO-2015109028 | A1 | | 7/2015 | |
| WO | WO-2017031068 | A1 | | 2/2017 | |
| WO | WO-2017081561 | A1 | | 5/2017 | |
| WO | WO-2019083989 | A1 | | 5/2019 | |
| WO | WO-2019140073 | A1 | | 7/2019 | |
| WO | WO-2020061143 | A1 | | 3/2020 | |
| WO | WO-2020097428 | A1 | | 5/2020 | |
| WO | WO-2021117021 | A1 | * | 6/2021 | ............ A61M 60/33 |

OTHER PUBLICATIONS

Atherton, et al., Diastolic Ventricular Interaction In Chronic Heart Failure, Lancet, 349(9067):1720-1724 (1997).

Bannon, et al., Anatomic Considerations for Central Venous Cannulation, 4 Risk Management and Healthcare Policy, 4:27-39 (2011).

Bilecen, et al., MR Angiography With Venous Compression, Radiology, 233(2):617-619 (Nov. 2004).

Delis, et al., Effect of Posture on Popliteal Artery Hemodynamics, 135(3):265-269 (Mar. 2000).

Difference Between Superior and Inferior Vena Cava, Pediaa (Aug. 28, 2018), https://pediaa.com/difference-between-superior-and-inferior-vena-cava/.

Extended EP Search Report dated Oct. 20, 2021 in EP Patent Application Serial No. 21177661.2 (0331).

Hansen, et al., Veno-occlusive unloading of the heart reduces infarct size in experimental ischemia-reperfusion, *Scientific Reports*, 11(1):1-9 (Feb. 2021).

Herrera, et al., First Percutaneous Transluminal Caval Flow Restriction in a Patient With Congestive Heart Failure, Abstract No. TCT-428, New Devices and Innovation, www.jacctctabstracts 2014.com, vol. 64/11/Suppl B, Sep. 13-17, 2014.

International Search Report & Written Opinion dated Jan. 28, 2019 in Int'l PCT Patent Appl. Serial No. PCT/US2018/057085 (0310).

International Search Report & Written Opinion dated Feb. 18, 2021 in Int'l PCT Patent Appl. Serial No. PCT/US2020/061386 (0410).

International Search Report & Written Opinion dated Oct. 18, 2016 in Int'l PCT Patent Application Serial No. PCT/US2016/047055 (0210).

Ishiguchi, et al., Endovascular Stent-Graft Deployment: Temporary Vena Caval Occlusion with Balloons to Control Aortic Blood Flow-Experimental Canine Study and Initial Clinical Experience, Radiology, 215:(2):594-599 (2000).

Kaiser, et al., First-in-Human Experience of Mechanical Preload Control in Patients With HFpEF During Exercise, *J. Am. Coll. Cardiol. Basic Trans. Science*, pp. 1-10 (2021), https://doi.org/10.1016/j.jacbts.2020.12.007.

Kappagoda, et al., Effect of Stimulating Right Atrial Receptors On Urine Floe In The Dog, J. Physiol, 235:493-502 (1973).

Kapur, et al., First-in-human experience with occlusion of the superior vena cava to reduce cardiac filling pressures in congestive heart failure, Catheter Cardiovasc. Interv., 93:1205-1210 (2019).

Kapur, et al., Intermittent Occlusion of the Superior Vena Cava Reduces Cardiac Filling Pressures in Preclinical Models of Heart Failure, Journal of Cardiovascular Translational Research, published on: Nov. 26, 2019, https://doi.org/1 0.1 007/s12265-019-09916-y.

Kass, et al., Use of a conductance (volume) catheter and transient inferior vena caval occlusion for rapid determination of pressure-vol. relationships in man, Cathet. Cardiovasc. Diagn., 15(3):192-202 (1988).

Lee et al., Partial right atrial inflow occlusion for controlled systemic hypotension during thoracic endovascular aortic repair, *J. Vasc. Surg.*, 48(2):494-498 (2008).

Low, Phillip A., "Venoarteriolar Reflex," Primer On The Autonomic Nervous System, Second Edition, Chapter 38, pp. 152-153 (2004).

Mehta, M.D., Manish, Compliant Occlusion Balloons—Use of complaint occlusion balloons during EVAR for AAA rupture, insert to *Endovascular Today*, pp. 29-31 (Nov. 2008).

(56) References Cited

OTHER PUBLICATIONS

Mork, et al., Impaired Neurogenic Control of Skin Perfusion In Erythromelalgia, Journal of Investigative Dermatology, 118(4):699-703 (Apr. 2002).
Moscucci, M., Grossman & Baim's Cardiac Catheterization, Angiography, and Intervention, 8th Edition, 2014.
Rachapalli, et al., Superior Vena Cava Syndrome: Role of the Interventionalist, Canadian Association of Radiologists Journal, 65:168-176 (2014).
Rodrigues, et al., Effect of baroreceptor denervation on the autonomic control of arterial pressure in conscious mice, Exp. Physiol., 96(9):853-862 (2011).
Rosenblum, et al., Conceptual Considerations For Device-Based Therapy in Acute Decompensated Heart Failure, Circulation: Heart Failure, 13(4):e006731 (Apr. 2020).
Ross, et al., Studies on Starling's Law of the Heart, IX. The Effects of Impeding Venous Return on Performance of the Normal and Failing Human Left Ventricle, Circulation, 30:719-727 (1964).
Shimizu, et al., Embolization of a Fractured Central Venous Catheter Placed Using The Internal Jugular Approach, International Journal of Surgery Case Reports, 5(5):219-221 (Jan. 2014).
Swan, et al., Catheterization Of The Heart In Man With Use Of A Flow-Directed Balloon-Tipped Catheter, New England Journal of Medicine, 283(9):447-451 (Aug. 1970).
Tucker, et al., Anatomy, Abdomen and Pelvis, Inferior Vena Cava, Jul. 27, 2021, available at https://www.ncbi.nlm.nih.gov/books/NBK482353/.
Tzifa, et al., Endovascular Treatment for Superior Vena Cava Occlusion or Obstruction in a Pediatric and Young Adult Population, A 22-Year Experience, Journal of the American College of Cardiology, 49(9):1003-1009 (2007).
Van Fossen, et al., Safety and efficacy of inferior vena caval occlusion to rapidly alter ventricular loading conditions in idiopathic dilated cardiomyopathy, The American Journal of Cardiology, 59(9):937-942 (1987).
Yancy, et al., 2013 ACCF/AHA Guideline for the Management of Heart Failure—A Report of the American College of Cardiology Foundation/American Heart Association Task Force on Practice Guidelines, Circulation, 128:e240-e327 (2013).

* cited by examiner

SYSTEMS AND METHODS FOR SELECTIVE OCCLUSION OF THE PERIPHERAL VENOUS VASCULATURE TO UNLOAD THE HEART

CROSS-REFERENCE TO RELATED APPLICATIONS

This application claims priority to U.S. Provisional Application Ser. No. 63/365,941, filed on Jun. 6, 2022, the entire contents of which are incorporated herein by reference.

FIELD OF USE

The present disclosure is directed to unloading the heart to improve cardiac function in patients suffering from heart failure, including patients with reduced ejection fraction, and for treating pulmonary hypertension.

BACKGROUND

Heart failure is a major cause of global mortality. Heart failure often results in multiple long-term hospital admissions, especially in the later phases of the disease. Absent heart transplantation, the long-term prognosis for such patients is bleak, and pharmaceutical approaches are palliative only. Consequently, there are few effective treatments to slow or reverse the progression of this disease.

Heart failure can result from any of multiple initiating events. Heart failure may occur as a consequence of ischemic heart disease, hypertension, valvular heart disease, infection, inherited cardiomyopathy, pulmonary hypertension, or under conditions of metabolic stress including pregnancy. Heart failure also may occur without a clear cause—also known as idiopathic cardiomyopathy. The term heart failure encompasses left ventricular, right ventricular, or biventricular failure.

While the heart can often initially respond successfully to the increased workload that results from high blood pressure or loss of contractile tissue, over time this stress induces compensatory cardiomyocyte hypertrophy and remodeling of the ventricular wall. In particular, over the next several months after the initial cardiac injury, the damaged portion of the heart typically will begin to remodel as the heart struggles to continue to pump blood with reduced muscle mass or less contractility. This in turn often leads to overworking of the myocardium, such that the cardiac muscle in the compromised region becomes progressively thinner, enlarged and further overloaded. Simultaneously, the ejection fraction of the damaged ventricle drops, leading to lower cardiac output and higher average pressures and volumes in the chamber throughout the cardiac cycle, the hallmarks of heart failure. Not surprisingly, once a patient's heart enters this progressively self-perpetuating downward spiral, the patient's quality of life is severely affected and the risk of morbidity skyrockets. Depending upon a number of factors, including the patient's prior physical condition, age, sex and lifestyle, the patient may experience one or several hospital admissions, at considerable cost to the patient and social healthcare systems, until the patient dies either of cardiac arrest or any of a number of co-morbidities including stroke, kidney failure, liver failure, or pulmonary hypertension.

Pharmaceutical approaches are available as palliatives to reduce the symptoms of heart failure, but there exists no pharmaceutical path to arresting or reversing heart failure. Moreover, the existing pharmaceutical approaches are systemic in nature and do not address the localized effects of remodeling on the cardiac structure. It therefore would be desirable to provide systems and methods for treating heart failure that can arrest, and more preferably, reverse cardiac remodeling that result in the cascade of effects associated with this disease.

Pulmonary hypertension (PH) is also a major cause of morbidity and mortality worldwide. While heart failure is a common cause of pulmonary hypertension, as mentioned above, pulmonary hypertension may also be caused by primary lung disease. Today, pharmacologic treatments may reduce pulmonary artery systolic pressure (PASP) and improve symptoms and ultimately survival for patients with pulmonary hypertension. However, there are drawbacks to pharmacologic treatments such as costs and side effects.

SUMMARY

The present disclosure overcomes the drawbacks of previously-known systems and methods by providing a system for unloading a heart of a patient to improve cardiac performance. The system may include a first flow limiting element that may be selectively actuated to occlude a first vein in fluid communication with a first extremity of the patient, a second flow limiting element that may be selectively actuated to occlude a second vein in fluid communication with a second extremity of the patient, and a controller operatively coupled to the first and second flow limiting elements. The controller may be programmed to cause the first and/or second flow limiting elements to expand according to a predetermined actuation regimen to selectively occlude the first and/or second veins to reduce cardiac preload and increase mean arterial pressure to thereby selectively increase arterial vascular resistance of the patient's extremities, while maintaining arterial vascular resistance of the patient's heart and end organs and increasing perfusion to the patient's heart and end organs.

In some embodiments, the first vein may be a contralateral iliac vein and the second vein may be an ipsilateral iliac vein. The system further may include a third flow limiting element operatively coupled to the controller, which may be selectively actuated to occlude a superior vena cava (SVC) of the patient. Accordingly, the controller may be programmed to cause the third flow limiting element to expand according to a second predetermined actuation regime to occlude the SVC and reduce cardiac preload. The system further may include a mechanical circulatory support (MCS) device.

The system further may include a third flow limiting element operatively coupled to the controller, which may be selectively actuated to occlude a contralateral subclavian vein of the patient, and a fourth flow limiting element operatively coupled to the controller, which may be selectively actuated to occlude an ipsilateral subclavian vein of the patient. Accordingly, the controller may be programmed to cause the third and/or fourth flow limiting elements to expand according to a second predetermined actuation regime to selectively occlude the contralateral and/or ipsilateral subclavian veins to reduce cardiac preload and increase mean arterial pressure to thereby selectively increase arterial vascular resistance of the patient's extremities, while maintaining arterial vascular resistance of the patient's heart and end organs and increasing perfusion to the patient's heart and end organs.

The system further may include a fifth flow limiting element operatively coupled to the controller, which may be selectively actuated to occlude a superior vena cava (SVC)

of the patient. Accordingly, the controller is configured to cause the fifth flow limiting element to expand according to a third predetermined actuation regime to occlude the SVC and reduce cardiac preload. The system further may include a catheter operatively coupled to the controller, wherein the first and second flow limiting elements are disposed on a distal region of the catheter.

In some embodiments, the first vein may be a superior vena cava (SVC) and the second vein may be an inferior vena cava (IVC). Accordingly, the system may include a first catheter operatively coupled to the controller, and a second catheter operatively coupled to the controller, wherein the first flow limiting element is disposed on a distal region of the first catheter, and the second flow limiting element is disposed on a distal region of the second catheter. The system further may include a mechanical circulatory support (MCS) device.

Moreover, the predetermined actuation regime may be programmed to: cause only the first flow limiting element to expand for a first time period; cause the first and second flow limiting elements to expand for a second time period after the first time period; cause only the second flow limiting element to expand for a third time period after the second time period; and cause the first and second flow limiting elements to expand for a fourth time period after the third time period. Accordingly, the predetermined actuation regime may be programmed to cause at least 70% occlusion of the first and second veins during a treatment period. The predetermined actuation regime may be programmed in the controller such that the first flow limiting element or the second flow limiting element, or both, maintains occlusion throughout a treatment session. Each occlusion period during a treatment session may be at least one minute.

The system further may include one or more sensors that may measure one or more parameters and generate one or more signals indicative of the one or more measured parameters. For example, a first sensor of the one or more sensors may be disposed proximal to the first flow limiting element and a second sensor of the one or more sensors may be disposed proximal to the second flow limiting element. Additionally, the controller may be programmed to adjust the predetermined actuation regime to selectively occlude the first and/or second veins responsive to the one or more signals indicative of the one or more measured parameters.

In accordance with another aspect of the present disclosure, a method for unloading a heart of a patient to improve cardiac performance is provided. The method may include positioning a first flow limiting element within a first vein in fluid communication with a first extremity of the patient; positioning a second flow limiting element within a second vein in fluid communication with a second extremity of the patient; and causing the first and/or second flow limiting elements to expand according to a predetermined actuation regime to selectively occlude the first and/or second veins to reduce cardiac preload and increase mean arterial pressure to thereby selectively increase arterial vascular resistance of the patient's extremities, while maintaining arterial vascular resistance of the patient's heart and end organs and increasing perfusion to the patient's heart and end organs. For example, causing the first and/or second flow limiting elements to expand according to the predetermined actuation regime may cause the first flow limiting element or the second flow limiting element, or both, to maintain occlusion throughout a treatment session.

In some embodiments, positioning the first flow limiting element within the first vein of the patient may include positioning the first flow limiting element within a contralateral iliac vein of the patient, and positioning the second flow limiting element within the second vein of the patient may include positioning the second flow limiting element within an ipsilateral iliac vein of the patient. The method further may include positioning a third flow limiting element within a contralateral subclavian vein of the patient; positioning a fourth flow limiting element within an ipsilateral subclavian vein of the patient; and causing the third and/or fourth flow limiting elements to expand according to a second predetermined actuation regime to selectively occlude the contralateral and/or ipsilateral subclavian veins to reduce cardiac preload and increase mean arterial pressure to thereby selectively increase arterial vascular resistance of the patient's extremities, while maintaining arterial vascular resistance of the patient's heart and end organs and increasing perfusion to the patient's heart and end organs.

Alternatively, the method may include positioning a third flow limiting element within a superior vena cava of the patient, and intermittently actuating the third flow limiting element according to a second predetermined actuation regime to occlude the SVC and reduce cardiac preload. The method further may include positioning a mechanical circulatory support (MCS) device within the patient's heart, and actuating the MCS device. In some embodiments, positioning the first flow limiting element within the first vein of the patient includes positioning the first flow limiting element within a superior vena cava (SVC) of the patient, and positioning the second flow limiting element within the second vein of the patient includes positioning the second flow limiting element within an inferior vena cava (IVC) of the patient.

DETAILED DESCRIPTION

Figure 1A:
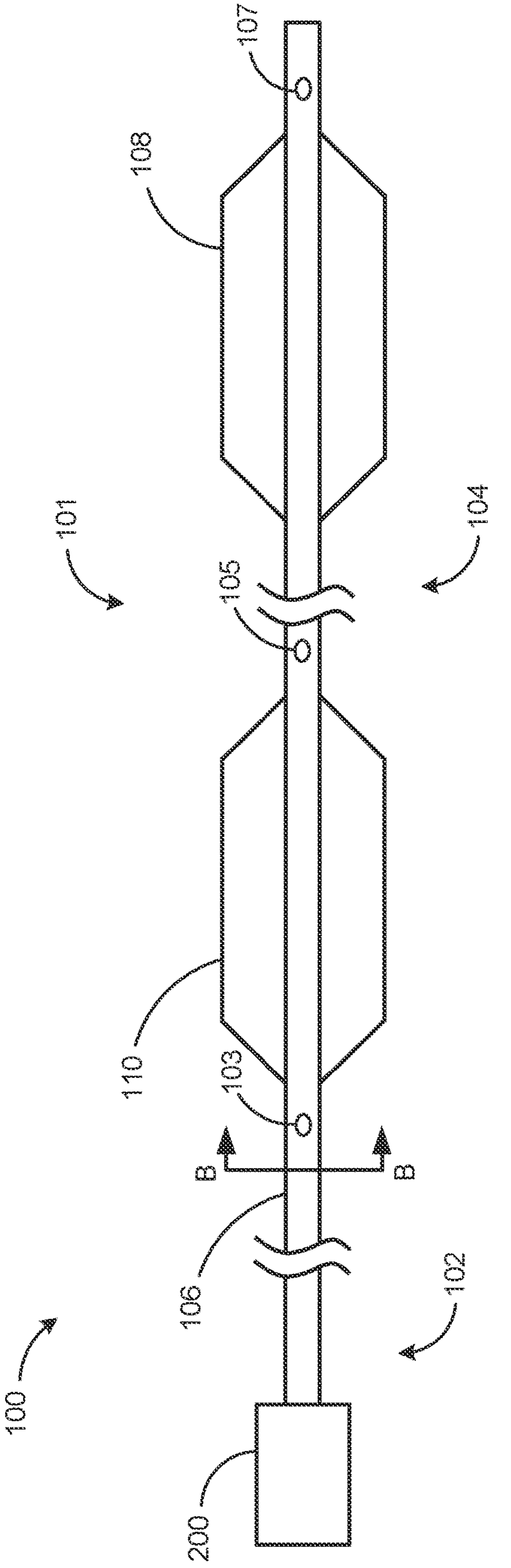
FIG. 1A illustrates an exemplary system for improving cardiac function including a dual balloon catheter constructed in accordance with the principles of the present disclosure.

In the human anatomy, deoxygenated blood returns to the heart through the vena cava, which comprises the superior vena cava and the inferior vena cava coupled to the right atrium of the heart. Blood moves from the right atrium through the tricuspid valve to the right ventricle, where it is pumped via the pulmonary artery to the lungs. Oxygenated blood returns from the lungs to the left atrium via the pulmonary vein. The oxygenated blood then enters the left ventricle, which pumps the blood through the aorta to the rest of the body.

Attempts have been made to address heart failure by treating various aspects of heart failure, but none appear either intended to, or capable of, reducing left ventricular end diastolic volume (LVEDV), left ventricular end diastolic pressure (LVEDP), left ventricular end diastolic diameter (LVEDD), right ventricular end diastolic volume (RVEDV), or right ventricular end diastolic pressure (RVEDP) without causing possibly severe side-effects. In view of the foregoing drawbacks of the previously known systems and methods for regulating venous return to address heart failure, it would be desirable to provide systems and methods for treating acute and chronic heart failure that reduce the risk of exacerbating co-morbidities associated with the disease, and that arrest or reverse cardiac remodeling. It would further be desirable to provide systems and methods for unloading the heart while increasing cardiac output and improving perfusion to the patient's heart.

In accordance with one aspect of the present disclosure, applicants have determined that controlling the return of venous blood to the right ventricle by intermittent venous occlusion beneficially lowers RVEDP, RVEDV, LVEDP, and LVEDV without adversely reducing left ventricular systolic pressure (LVSP). It is theorized that selective intermittent occlusion of the venous vasculature will further reduce the risk of worsening congestion of the kidneys. Congestion of the kidneys may impair renal function due to volume overload and neurohormonal activation in patients with heart failure. Volume overload may occur where the weakened heart cannot pump as much blood, which leads to less blood flow through the kidneys. With less blood flow through the kidneys, less blood is filtered by the kidneys and less water is released via urination causing excess volume to be retained in the body. With the excess volume, the heart pumps with increasingly less efficiency and the patient ultimately spirals toward death as the body becomes progressively more congested.

By reducing flow into the right atrium, volume within the left ventricle is ultimately reduced, permitting the muscle fibers to stretch within a normal range, naturally increasing contractility and allowing the heart to drive more fluid to the kidneys. The kidneys may then extract water, which may be removed from the body through urination. It is further understood that during venous occlusion, e.g., SVC occlusion, a negative pressure sink is created in the right atrium caused by an abrupt reduction in right atrial pressure and volume, for example, as described in U.S. Pat. No. 10,842,974 to Kapur et al., the entire contents of which are incorporated herein by reference. As a result, flow from the renal vein may be accelerated thereby enhancing renal decongestion and promoting blood flow across the kidney, increasing urine output. Accordingly, venous occlusion may benefit patients with heart failure by reducing cardiac and pulmonary pressures and promoting decongestion.

Applicant understands that intermittent occlusion of the venous vasculature (i.e., cardio-pulmonary unloading) over a period of time (e.g., minutes, hours, days, weeks, or months) will beneficially permit a patients' heart to discontinue or recover from remodeling of the myocardium. The systems described herein enable the myocardium to transition from pressure-stroke volume curve indicative of heart failure towards a pressure-stroke volume curve more closely resembling that of a healthy heart.

In general, the system and methods of the present disclosure may be used to treat any disease to improve cardiac function by arresting or reversing myocardial remodeling, and particularly those conditions in which a patient suffers from heart failure. Such conditions include but are not limited to, e.g., systolic heart failure, diastolic (non-systolic) heart failure, decompensated heart failure patients in (ADHF), chronic heart failure, acute heart failure and pulmonary hypertension, heart attacks, heart failure with preserved ejection fraction, right heart failure, constrictive and restrictive cardiomyopathies, and cardio-renal syndromes (Types 1-5). The system and methods of the present invention also may be used as a prophylactic to mitigate the aftermath of acute right or left ventricle myocardial infarction, pulmonary hypertension, RV failure, post-cardiotomy shock, or post-orthotopic heart transplantation (OHTx) rejection, or otherwise may be used for cardiorenal applications and/or to treat renal dysfunction, hepatic dysfunction, or lymphatic congestion. Also, the system and methods of the present disclosure may reduce hospital stays caused by various ailments described herein, including at least acute exacerbation.

The relationship between left ventricular pressure or left ventricular volume and stroke volume is often referred to as the Frank-Starling relationship, or "Starling curve". That relationship states that cardiac stroke volume is dependent on preload, contractility, and afterload. Preload refers to the volume of blood returning to the heart; contractility is defined as the inherent ability of heart muscle to contract; and afterload is determined by vascular resistance and impedance. In heart failure due to diastolic or systolic dysfunction, reduced stroke volume leads to increased volume and pressure increase in the left ventricle, which can result in pulmonary edema. Increased ventricular volume and pressure also results in increased workload and increased myocardial oxygen consumption. Such over-exertion of the heart results in worsening cardiac function as the heart becomes increasingly deprived of oxygen due to supply and demand mismatch. Furthermore, as volume and pressure build inside the heart, contractile function worsens due to stretching of cardiac muscle. This condition is termed "congestive heart failure."

In a typical Starling curve for a normal heart, stroke volume increases with increasing LVEDP or LVEDV, and begins to flatten out, i.e., the slope of the curve decreases, only at very high pressures or volumes. A patient who has just experienced an acute myocardial infarction (AMI) will exhibit reduced stroke volume at every value of LVEDV or LVEDP. However, because the heart has just begun to experience the overload caused by the localized effect of the infarct, myocardial contractility of the entire ventricle is still relatively good, and stroke volume is still relatively high at low LVEDP or LVEDV. By contrast, a patient who has suffered from cardiac injury in the past may experience progressive deterioration of cardiac function as the myocardium remodels over time to compensate for the increased workload and reduced oxygen availability. As noted above, this can lead to progressively lower stroke volume as the ventricle expands due to generally higher volume and pressure during every phase of the cardiac cycle. Accordingly, the stroke volume continues to decline as the LVEDP or LVEDV climb, until eventually the heart gives out or the patient dies of circulatory-related illness.

For a normal heart, as the end-diastolic volume increases, the stroke volume increases. For a healthy heart, however, beyond a certain point, increased end-diastolic volume no longer results in increased stroke volume, and continued increases in end-diastolic volume do not result in further increases in stroke volume. By contrast, for patients with heart failure, further increases in end-diastolic volume do not result in a substantially flat stroke volume, but instead stroke volume decreases. Accordingly, increasing EDV for patients with HF results in further reduction in SV, leading to a downward spiral in heart function, and ultimately death. A phenomenon referred to as "diastolic ventricular interaction" arises in part due to the structural arrangement of the cardiac chambers. As discussed, for example, in an article entitled "Diastolic ventricular interaction in chronic heart failure," Lancet 1997; 349:1720-24 by J. Atherton et al., the pericardium constrains the extent to which the ventricles of a failing heart can expand. Consequently, as right ventricular end diastolic volume increases, it necessarily causes a reduction in the end diastolic volume of the left ventricle. As reported in that article, reduction in right ventricular diastolic filling caused by external lower body suction allows augmented left ventricular diastolic filling.

Applicant understands that the foregoing phenomenon can advantageously be utilized in the context of the present disclosure to improve cardiac performance. In particular, in heart failure and the presence of pulmonary hypertension, right ventricular congestion due to increased volume overload can push the interventricular septum towards the left ventricular cavity, thereby reducing LV stroke volume and cardiac output. By occluding venous flow to the right atrium, right ventricular pressure and volume are reduced. This in turn will shift the interventricular septum away from the LV cavity, allowing for increased left ventricular stroke volume and enhanced cardiac output. For these reasons, venous occlusion in accordance with the principles of the present disclosure may favorably alter diastolic ventricular interaction and enhance cardiac output. Specifically, with respect to diastolic heart failure, venous occlusion in accordance with the principles of the present invention may provide a reduction in cardiac filling pressures, increased LV relaxation (tau), increased LV capacitance, increased lusitropy, reduced LV stiffness, and reduced cardiac strain. The systems and methods of inducing intermittent venous occlusion of the present disclosure to reduce the volume and hence pressure of blood entering the right ventricle for patients in HF, and which must then be pumped by the left ventricle, reduces the workload and wall stress in the myocardium throughout the cardiac cycle, reduces myocardial oxygen consumption, and improves contractile function. This improves heart function by moving a patient's heart contractility toward a healthy range of the patient's Frank-Starling curve.

Figure 1B:
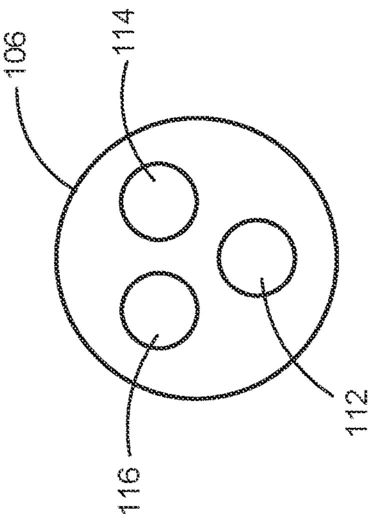
FIG. 1B is a cross-sectional view of the catheter of the system of FIG. 1A.

Referring now to FIGS. 1A and 1B, exemplary system 100 for venous occlusion is provided. System 100 includes balloon catheter 101, which includes catheter 106 having proximal region 102 coupled to controller 200 and distal region 104, and one or more independently actuatable flow limiting elements, e.g., first flow limiting element 108 and second flow limiting element 110, disposed on distal region 104. First and second flow limiting elements 108, 110 are fluidicly coupled to controller 200, which is programmed to independently and intermittently actuate first and second flow limiting elements 108, 110, e.g., in accordance to a predetermined actuation regimen stored in a memory of controller 200.

As shown in FIG. 1A, second flow limiting element 110 is disposed on catheter 106 proximal to first flow limiting element 108. First and second flow limiting elements 108, 110 may be sufficiently spaced apart along catheter 106, such that first flow limiting element 108 may be disposed in a first portion of a vein, e.g., the contralateral side of the vein, and second flow limiting element 110 may be disposed in a second portion of the same vein, e.g., the ipsilateral side of the same vein. For example, first flow limiting element 108 may be sized and shaped to be disposed in a contralateral iliac vein while second flow limiting element 110 may be sized and shaped to be disposed in an ipsilateral iliac vein. Moreover, first flow limiting element 108 may be sized and shaped to be disposed in a contralateral subclavian vein while second flow limiting element 110 may be sized and shaped to be disposed in an ipsilateral subclavian vein, as described in further detail below.

In addition, system 100 may include one or more sensors, e.g., sensors 103, 105, 107, for measuring one or more parameters across system 100, e.g., heart rate, blood flow rate, blood volume, and/or pressure including cardiac filling pressure, and generating signals indicative of the measured parameters. For example, sensor 103 may be disposed on catheter 106 proximal to second flow limiting element 110, sensor 105 may be disposed on catheter 106 between first and second flow limiting elements 108, 110, and sensor 107 may be disposed on catheter 106 distal to first flow limiting element 108, as shown in FIG. 1A. Alternatively, the one or more sensors may be one or more fluid columns within catheter 106, such that pressure may be measured at proximal region 102 of catheter 106. Sensor 105 may be used to determine the extent of occlusion caused by second flow limiting element 110, for example, by monitoring the pressure drop across second flow limiting element 110, and sensor 107 may be used to determine the extent of occlusion caused by first flow limiting element 108, for example, by monitoring the pressure drop across first flow limiting element 108.

Catheter 106 may include a flexible tube. Distal region 104 of catheter 106 may be configured for placement in a venous vasculature of the patient, e.g., the iliac vein, the subclavian vein, the SVC, or the IVC, as described in further detail below. The distal end of catheter 106 may include a tapered, atraumatic tip. As shown in FIG. 1A, first and second flow limiting elements 108, 110 are illustratively expandable balloons that are capable of transitioning between a contracted state, allowing transluminal placement and an expanded, deployed state, to thereby selectively impede blood flow into the right atrium of the patient. First and second flow limiting elements 108, 110 may be sized and shaped to fully occlude the target vein in the expanded state. In addition, catheter 106 may include an anchoring mechanism configured to anchor flow distal region 104 the target venous vasculature. For example, the anchoring mechanism may be contractible for delivery in a contracted state and expandable upon release from a delivery device, e.g., a sheath. The anchoring mechanism may be coupled to catheter 106 proximal to second flow limiting element 110, between first and second flow limiting elements 108, 110, or distal to first flow limiting element 108, or a combination thereof.

Figure 2:
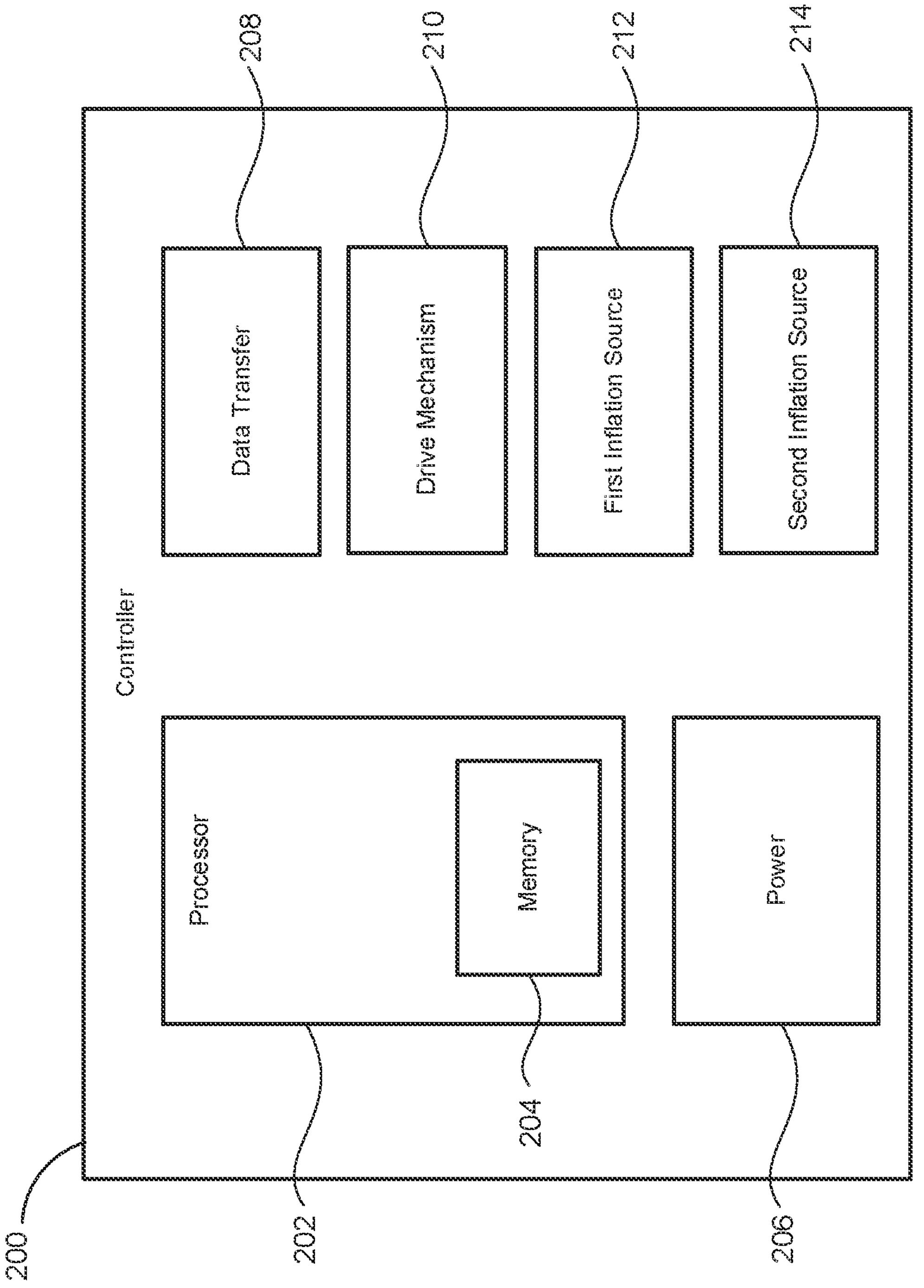
FIG. 2 illustrates some example components that may be included in the controller of the system of FIG. 1A.

Referring now to FIG. 2, exemplary controller 200 is provided. Controller 200 may house drive mechanism 220 (e.g., motor, pump) for actuating first and second flow limiting elements 108, 110, processor 202 programmed to control signals to drive mechanism 210, and additional optional sensors for monitoring a physiologic parameter of the patient, such as heart rate or blood pressure. Controller 200 may include or be fluidicly coupled to a source of inflation medium (e.g., gas or fluid), e.g., first inflation source 212 fluidicly coupled to first flow limiting element 108 and second inflation source 214 fluidicly coupled to second flow limiting element 110. Drive mechanism 210 may be actuated to transfer the inflation medium between first and second inflation sources 212, 214 and first and second flow limiting elements 108, 110, respectively, responsive to commands from processor 202.

As shown in FIG. 1B, catheter 106 may include first inflation lumen 114 for fluidicly coupling first flow limiting element 108 with first inflation source 212, and second inflation lumen 116 for fluidicly coupling second flow limiting element 110 with second inflation source 214. The proximal ends of first inflation lumen 114 and second inflation lumen 116 may each be connected to a side-arm tube which terminates in, e.g., a 3-way stopcock or a standard Luer lock fitting. Each side-arm tube may have a clamp configured to enable/disable flow through the respective lumen. Moreover, proximal region 102 of catheter 106 may include a hub that may be secured to the patient, e.g., via suture holes integrated in the hub or through holes compatible with stat-lock. Moreover, catheter 106 may include guidewire lumen 112 sized and shaped to receive a guidewire therethrough, to facilitate delivery of distal region 104 of catheter 106 to the target location within the patient's venous vasculature.

When either one, or both, of first and second flow limiting elements 108, 110 are inflated with inflation medium, they partially or fully occlude venous blood flow through the patient's respective vein, and when the inflation medium is withdrawn, first and/or second flow limiting elements 108, 110 deflate to remove the occlusion, thereby permitting flow to resume in the respective vein. The flow limiting elements may each be a balloon that preferably comprises a compliant or semi-compliant material, e.g., nylon, which permits the degree of expansion of the balloon to be adjusted to effectuate the desired degree of partial or complete occlusion of the venous vasculature. In addition, catheter 106, when partially external, provides a fail-safe design, in that the flow limiting elements only can be inflated to provide occlusion when the proximal end of catheter 106 is coupled to controller 200. Such a quick-disconnect coupling at proximal region 102 permits catheter 106 to be rapidly disconnected from controller 200 for cleaning and/or emergency.

Referring again to FIG. 2, controller 200 preferably also includes power supply 206 (e.g., battery) that provides the power needed to operate processor 202, data transfer circuit 208, and drive mechanism 210. Power supply 206 may be charged via an external power source, e.g., transcutaneously via respective inductive coils when controller 200 is implanted. Controller 200 may be sized and of such a weight that it can be worn in a harness under the patient's clothing, so that the system can be used while the patient is ambulatory, or such that controller 200 may be implanted within the patient. As discussed herein below, processor 202 includes memory 204 for storing computer software for operating controller 200. Controller 200 may be configured for implantation at a suitable location within the patient, e.g., subcutaneously under the clavicle. In such an embodiment, the implantable controller is configured for bidirectional communication with an external controller, e.g., a computing device or system-specific device. An external controller may be used to charge the battery of the implantable controller, e.g., via respective inductive coils in or coupled to each controller, and may receive data indicative of the sensed parameters resulting from the patient's ambulatory activity including heart rate, blood flow rate, blood volume, pressure including cardiac filling pressure.

Processor 202 may be programmed to maintain partial or full venous occlusion for a preset number of cardiac cycles in accordance with predetermined actuation regimen determined at the time of initial implantation of the catheter. For example, the predetermined actuation regimen may cause only first flow limiting element 108 to expand for a first time period, cause both first and second flow limiting elements 108, 110 to expand for a second time period after the first time period, cause first flow limiting element 108 to deflate such that only second flow limiting element 110 is expanded for a third time period after the second time period, and cause both first and second flow limiting elements 108, 110 to expand for a fourth time period after the third time period. The predetermined actuation regimen may be repeated throughout the treatment session. Accordingly, during the treatment session in accordance with the predetermined actuation regimen, at least one or both of first flow limiting element 108 and second flow limiting element 110 will be expanded throughout the treatment session, thereby providing at least 70-90%, or preferably at least 80%, overall occlusion throughout the treatment session, to thereby effectively reduce preload.

Each of the first, second, third, and fourth time periods may be between 1-15 minutes, or preferably 5-10 minutes. For example, the predetermined actuation regimen may cause only first flow limiting element 108 to expand for five minutes, then cause both first and second flow limiting elements 108, 110 to expand for five minutes, then cause only second flow limiting element 110 to expand for five minutes, and then cause both first and second flow limiting elements 108, 110 to expand for five minutes.

In one embodiment, data transfer circuit 208 monitors an input from an external sensor, e.g., sensors 103, 105, 107 positioned on catheter 200, and provides that signal to processor 200. Processor 200 may be programmed to receive the input from data transfer circuit 208 and adjust the interval during which first and second flow limiting elements 108, 110 are maintained in the expanded state, or to adjust the degree of occlusion caused by first and second flow limiting elements 108, 110. Thus, for example, sensors 103, 105, 107 disposed on catheter 106 may measure parameters, e.g., heart rate, blood flow rate, blood volume, pressure including cardiac filling pressure and central venous pressure. The output of sensors 103, 105, 107 is relayed to data transfer circuit 208 of controller 200, which may pre-process the input signal, e.g., decimate and digitize the output of the sensors, before it is supplied to processor 202. The signal provided to processor 202 allows for assessment of the effectiveness of the flow limiting elements, e.g., by showing reduced venous pressure during occlusion and during patency, and may be used by the patient or clinician to determine how much occlusion is required to regulate venous blood return based on the severity of congestion in the patient.

As another example, at least one of sensors 103, 105, 107 may be one or more electrodes for sensing the patient's heart rate. It may be desirable to adjust the predetermined actuation regimen, e.g., the interval during which venous occlusion by each flow limiting element is maintained, responsive to the patient's ambulatory activities, which typically will be reflected in the patient's hemodynamic state by a sensed physiological parameter(s), e.g., heart rate, blood flow rate, blood volume, pressure including cardiac filling pressure and/or central venous pressure. Accordingly, the electrodes may provide a signal to data transfer circuit 208, which in turn processes that signal for use by the programmed routines run by processor 202. For example, if the occlusion by first flow limiting element 108 is maintained for a time programmed during initial system setup so that flow limiting element is deployed for 15 minutes and then released for five minutes before being re-expanded, it may be desirable to reduce the occluded time interval to 10 minutes or more depending upon the level of physical activity of the patient, as detected by a change in heart rate, blood flow rate, blood volume, pressure including cardiac filling pressure and/or central venous pressure above or below predetermined thresholds. Sensor inputs provided to data transfer circuit 208, such as hemodynamic state, also may be used to adjust the duty cycle of the flow limiting elements responsive to the patient's detected level of activity. In addition, processor 202 may be programmed to maintain partial or full occlusion in the respective vein for a preset number of cardiac cycles after adjustment to the predetermined occlusion interval is made.

Data transfer circuit 208 also may be configured to provide bi-directional transfer of data, for example, by including wireless circuitry to transfer data from controller 200 to an external unit for display, review or adjustment. For example, data transfer circuit 208 may include Bluetooth circuitry that enables controller 200 to communicate with an external controller, e.g., a patient's computing device such as a smartphone, laptop, smartwatch, or tablet on which a special-purpose application has been installed to communicate and/or control controller 200. In this manner, controller 200 may send information regarding functioning of the system directly to the computing device for display of vital physiologic or system parameters using a suitably configured mobile application. In addition, the patient may review the data displayed on the screen of the computing device and determine whether he or she needs to seek medical assistance to address a malfunction or to adjust the system parameters. Further, the mobile application resident on the computing device may be configured to automatically initiate an alert to the clinician's monitoring service via the cellular telephone network.

Figure 3:
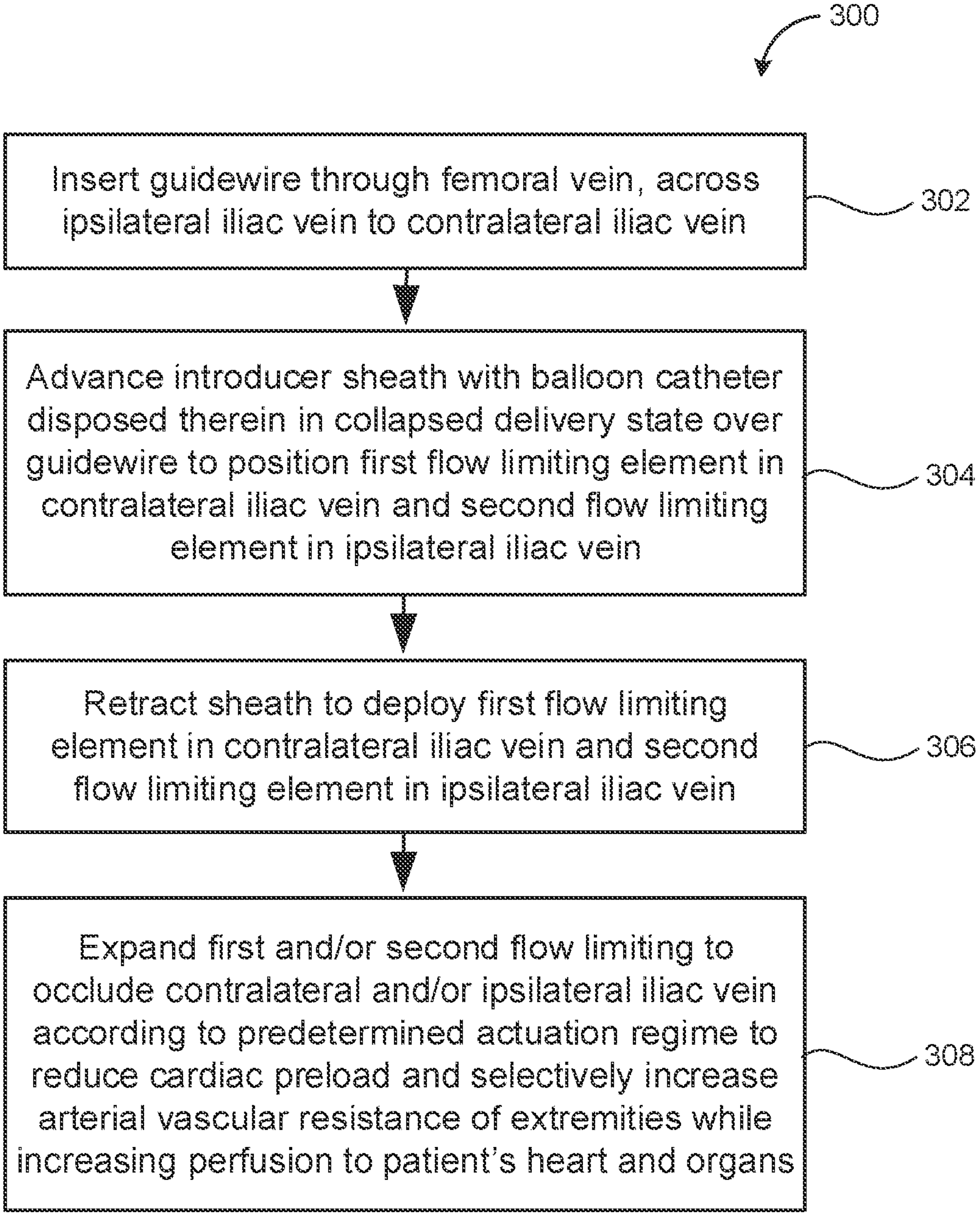
FIG. 3 is a flow chart illustrating exemplary steps for operating the system of FIG. 1A within the contralateral and ipsilateral iliac veins to improve cardiac performance in accordance with the principles of the present disclosure.

Referring now to FIG. 3, exemplary method 300 for delivering and operating system 100 of FIG. 1A within the patient's common iliac vein to improve cardiac performance is provided. Some of the steps of method 300 may be further elaborated by referring to FIGS. 4A to 4D. At step 302, a guidewire may be inserted into the patient through the femoral vein, up the femoral vein towards the common iliac vein, and across the common iliac vein on the ipsilateral side to the contralateral side of the common iliac vein. At step 304, catheter 106 may be inserted into an introducer sheath, such that first and second flow limiting elements 108, 110 are in their collapsed delivery state within the sheath. The introducer sheath and balloon catheter 101 disposed therein may then be advanced over the guidewire, e.g., via guidewire lumen 112 of catheter 106, until first flow limiting element 108 is positioned within the contralateral iliac vein and second flow limiting element 110 is positioned within the ipsilateral iliac vein, within the sheath. The guidewire may then be removed from catheter 106. Guidewire lumen 112 may be flushed prior to closing guidewire lumen 112 via a cap or clamp on a side-arm coupled to guidewire lumen 112. The proximal end of catheter 106 may then be coupled to controller 200, such that first inflation lumen 114 is coupled to first inflation source 212 and second inflation lumen 116 is coupled to second inflation source 214.

At step 306, the sheath may be retracted relative to catheter 106, such that first flow limiting element 108 is deployed within the contralateral iliac vein and second flow limiting element 110 is deployed within the ipsilateral iliac vein. At step 308, first and second flow limiting elements 108, 110 may be actuated via controller 200 to expand within the respective portions of the common iliac vein in accordance with the predetermined actuation regimen, to intermittently occlude the blood flow through the contralateral and ipsilateral iliac veins to thereby reduce cardiac preload and selectively increase arterial vascular resistance of extremities of the patient in fluid communication with the occluded veins while increasing perfusion to the patient's hearts and organs.

Figure 4A:
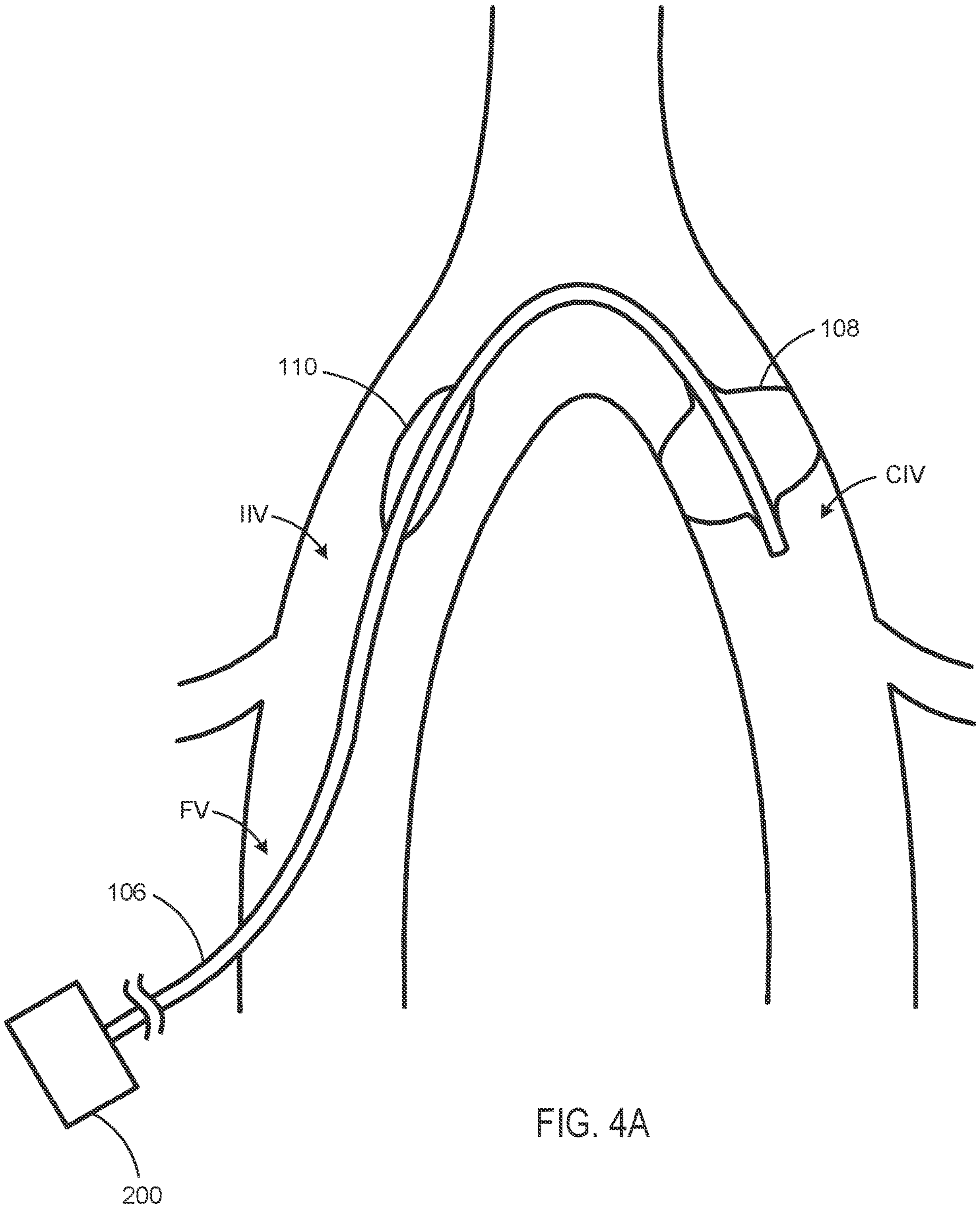
FIGS. 4A to 4D illustrate operation of the system of FIG. 1A within the contralateral and ipsilateral iliac veins in accordance with the principles of the present disclosure.
Figure 4B:
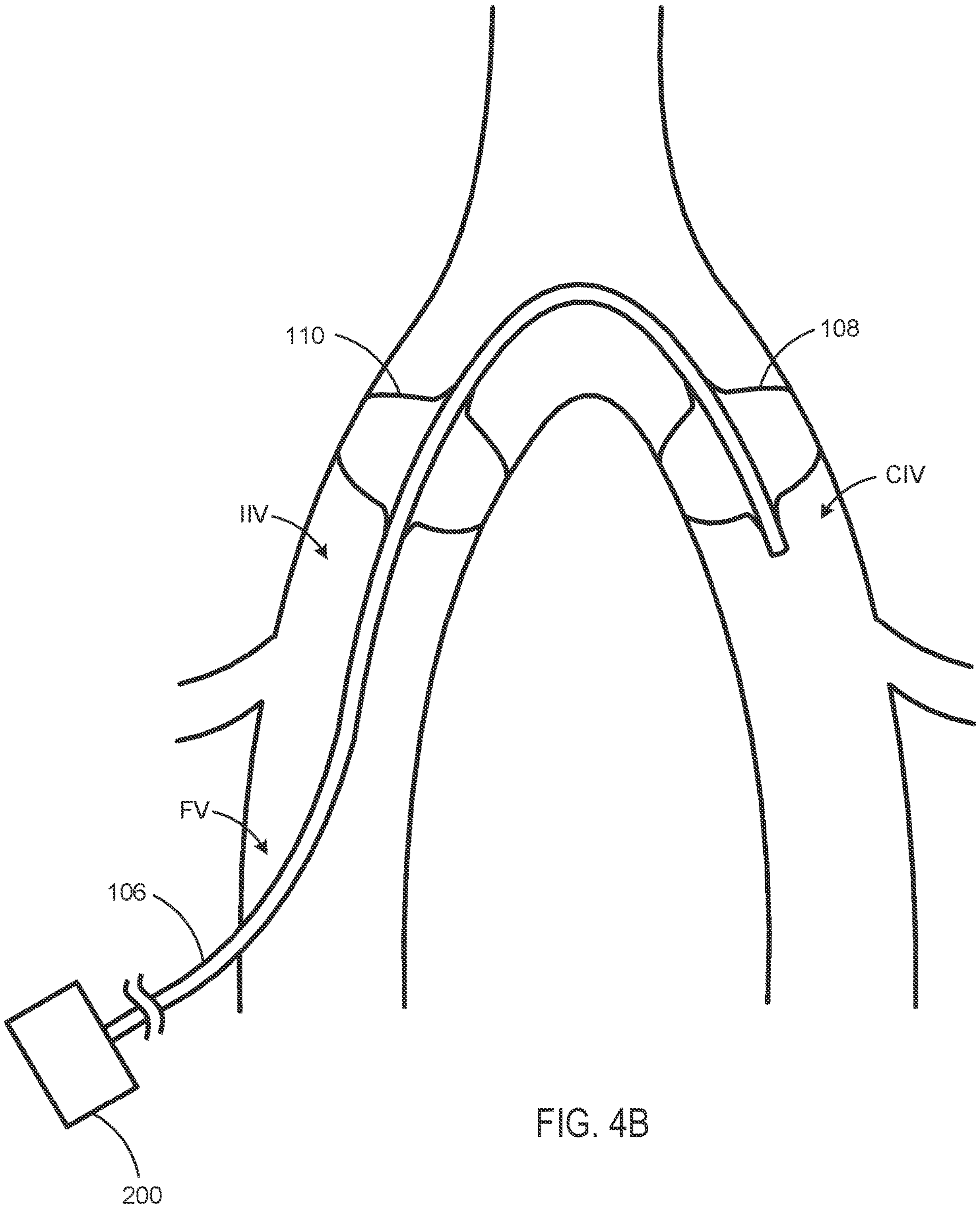
Figure 4C:
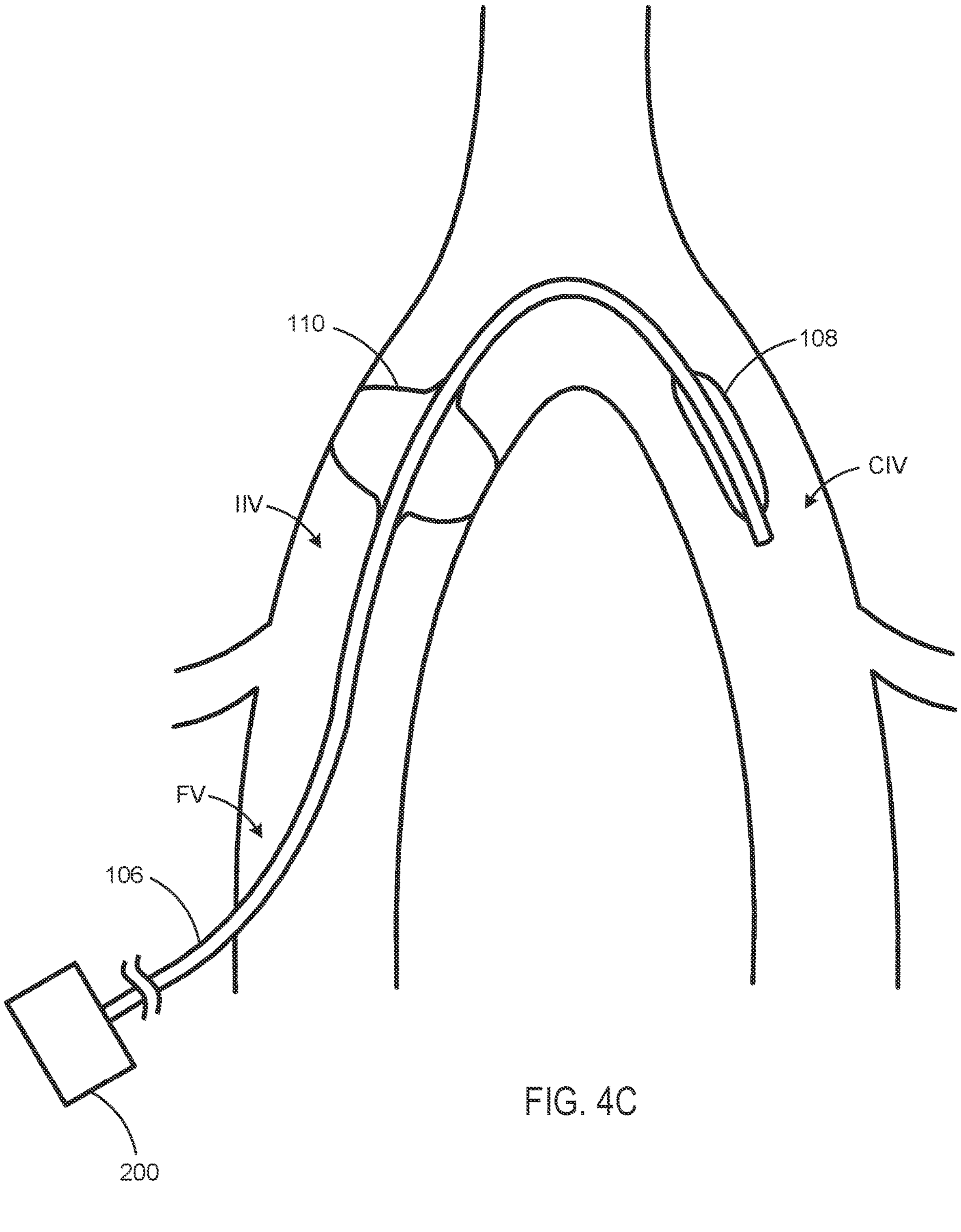
Figure 4D:
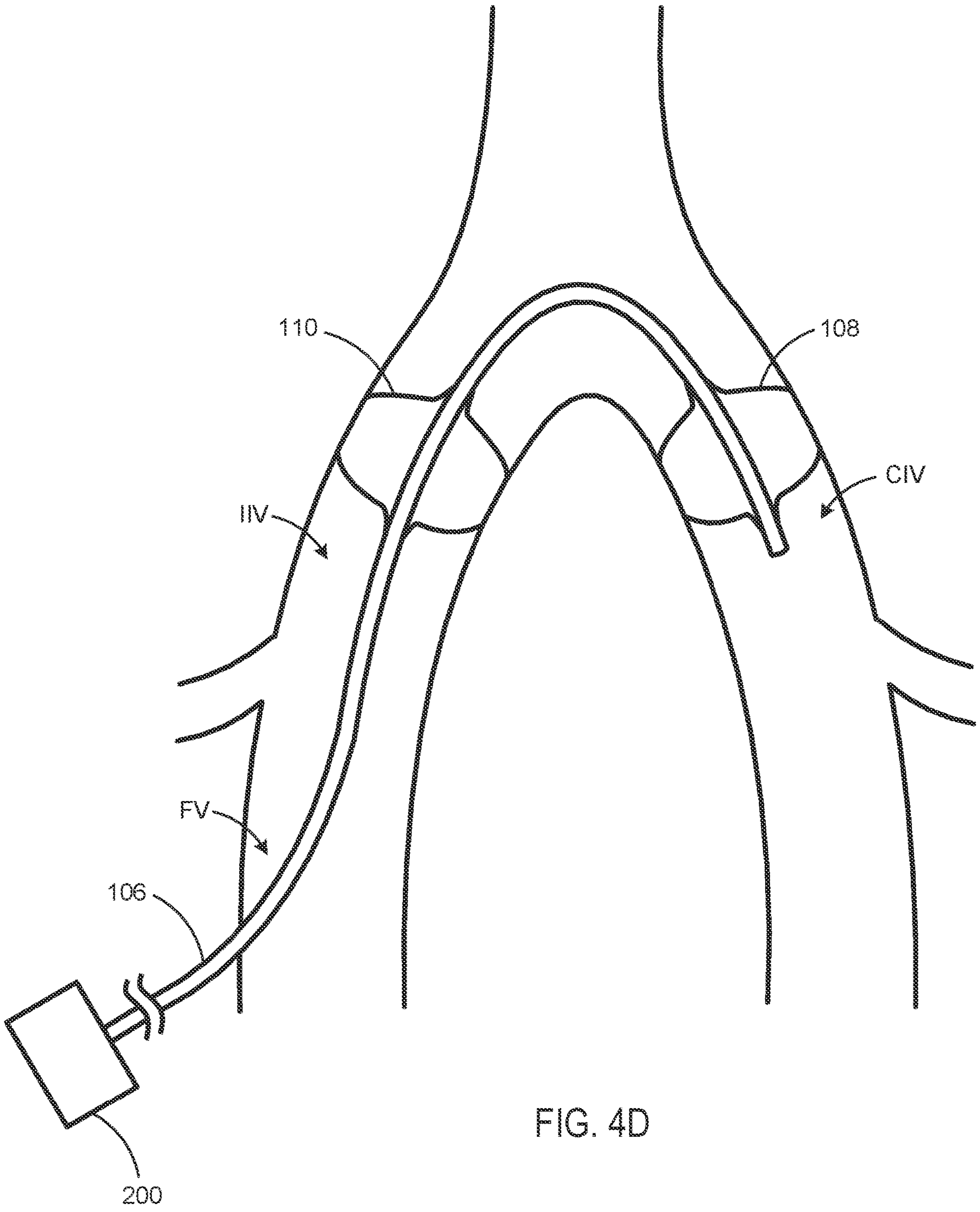

For example, for a first time period, e.g., five minutes, the predetermined actuation regimen may cause only first flow limiting element 108 to expand within the contralateral iliac vein, as shown in FIG. 4A. For a second time period, e.g., five minutes, following the first time period, the predetermined actuation regimen may cause both first and second flow limiting elements 108, 110 to expand within the contralateral and ipsilateral iliac veins, respectively, as shown in FIG. 4B. For a third time period, e.g., five minutes, following the second time period, the predetermined actuation regimen may cause first flow limiting element 108 to deflate, such that only second flow limiting element 110 remains expanded within the ipsilateral iliac vein, as shown in FIG. 4C. For a fourth time period, e.g., five minutes, following the third time period, the predetermined actuation regimen may cause both first and second flow limiting elements 108, 110 to expand within the contralateral and ipsilateral iliac veins, respectively, as shown in FIG. 4D. This actuation pattern may be repeated throughout the treatment session. Accordingly, for a fifth time period, e.g., five minutes, following the fourth time period, the predetermined actuation regimen may cause second flow limiting element 110 to deflate, such that only first flow limiting element 108 remains expanded within the contralateral iliac vein, and so on.

Figure 5:
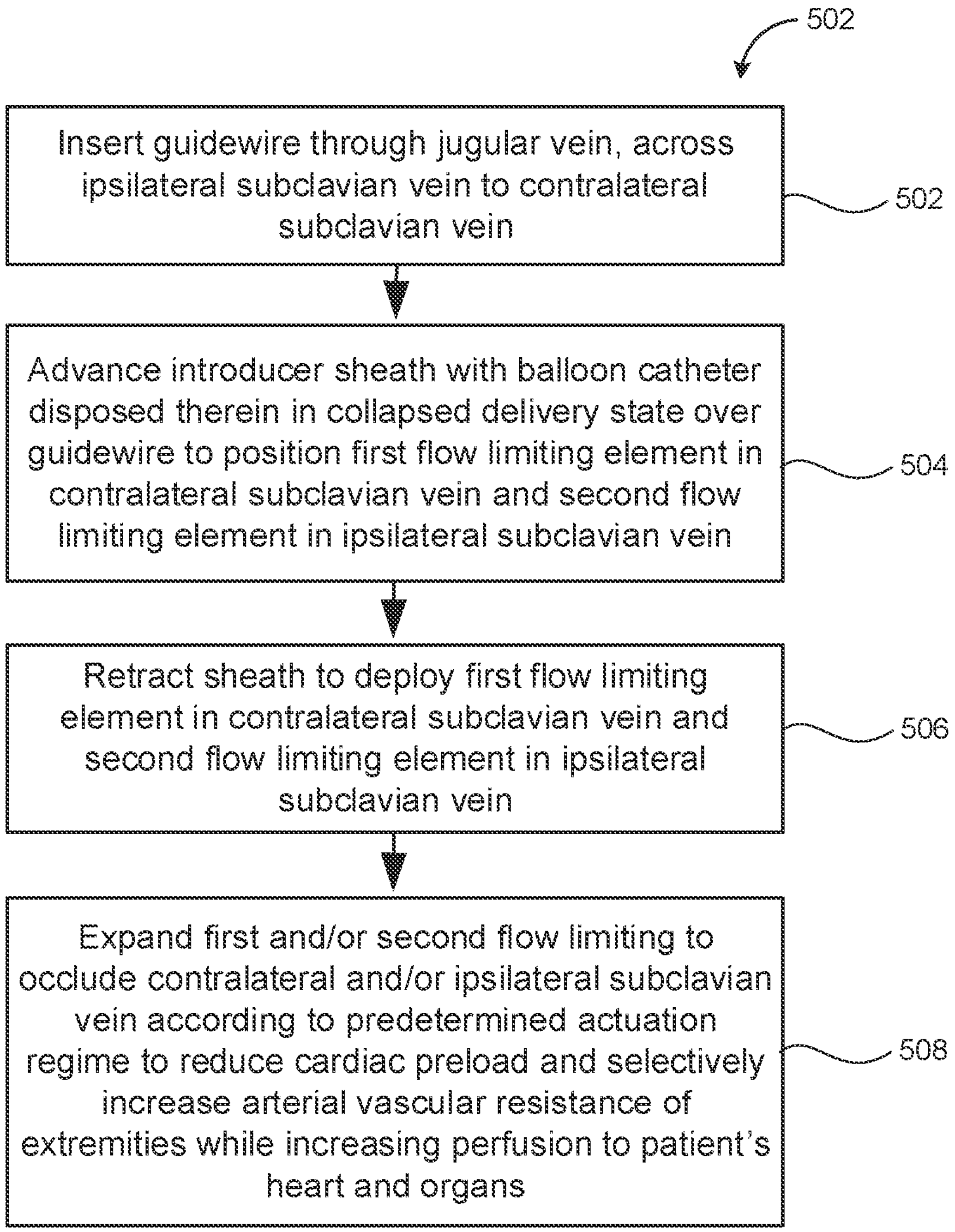
FIG. 5 is a flow chart illustrating exemplary steps for operating the system of FIG. 1A within the contralateral and ipsilateral subclavian veins to improve cardiac performance in accordance with the principles of the present disclosure.

Referring now to FIG. 5, exemplary method 500 for delivering and operating system 100 of FIG. 1A within the patient's subclavian vein to improve cardiac performance is provided. Some of the steps of method 500 may be further elaborated by referring to FIGS. 6A to 6D. At step 502, a guidewire may be inserted into the patient through the jugular vein, down the jugular vein towards the subclavian vein, and across the subclavian vein on the ipsilateral side to the contralateral side of the subclavian vein. At step 504, catheter 106 may be inserted into an introducer sheath, such that first and second flow limiting elements 108, 110 are in their collapsed delivery state within the sheath. The introducer sheath and balloon catheter 101 disposed therein may then be advanced over the guidewire, e.g., via guidewire lumen 112 of catheter 106, until first flow limiting element 108 is positioned within the contralateral subclavian vein and second flow limiting element 110 is positioned within the ipsilateral subclavian vein, within the sheath. The guidewire may then be removed from catheter 106. As described above, guidewire lumen 112 may be flushed prior to closing guidewire lumen 112 via a cap or clamp on a side-arm coupled to guidewire lumen 112, and the proximal end of catheter 106 may then be coupled to controller 106, such that first inflation lumen 114 is coupled to first inflation source 212 and second inflation lumen 116 is coupled to second inflation source 214.

At step 506, the sheath may be retracted relative to catheter 106, such that first flow limiting element 108 is deployed within the contralateral subclavian vein and second flow limiting element 110 is deployed within the ipsilateral subclavian vein. At step 508, first and second flow limiting elements 108, 110 may be actuated via controller 200 to expand within the respective portions of the subclavian vein in accordance with the predetermined actuation regimen, to intermittently occlude the blood flow through the contralateral and ipsilateral subclavian veins to thereby reduce cardiac preload and selectively increase arterial vascular resistance of extremities of the patient in fluid communication with the occluded veins while increasing perfusion to the patient's hearts and organs.

Figure 6A:
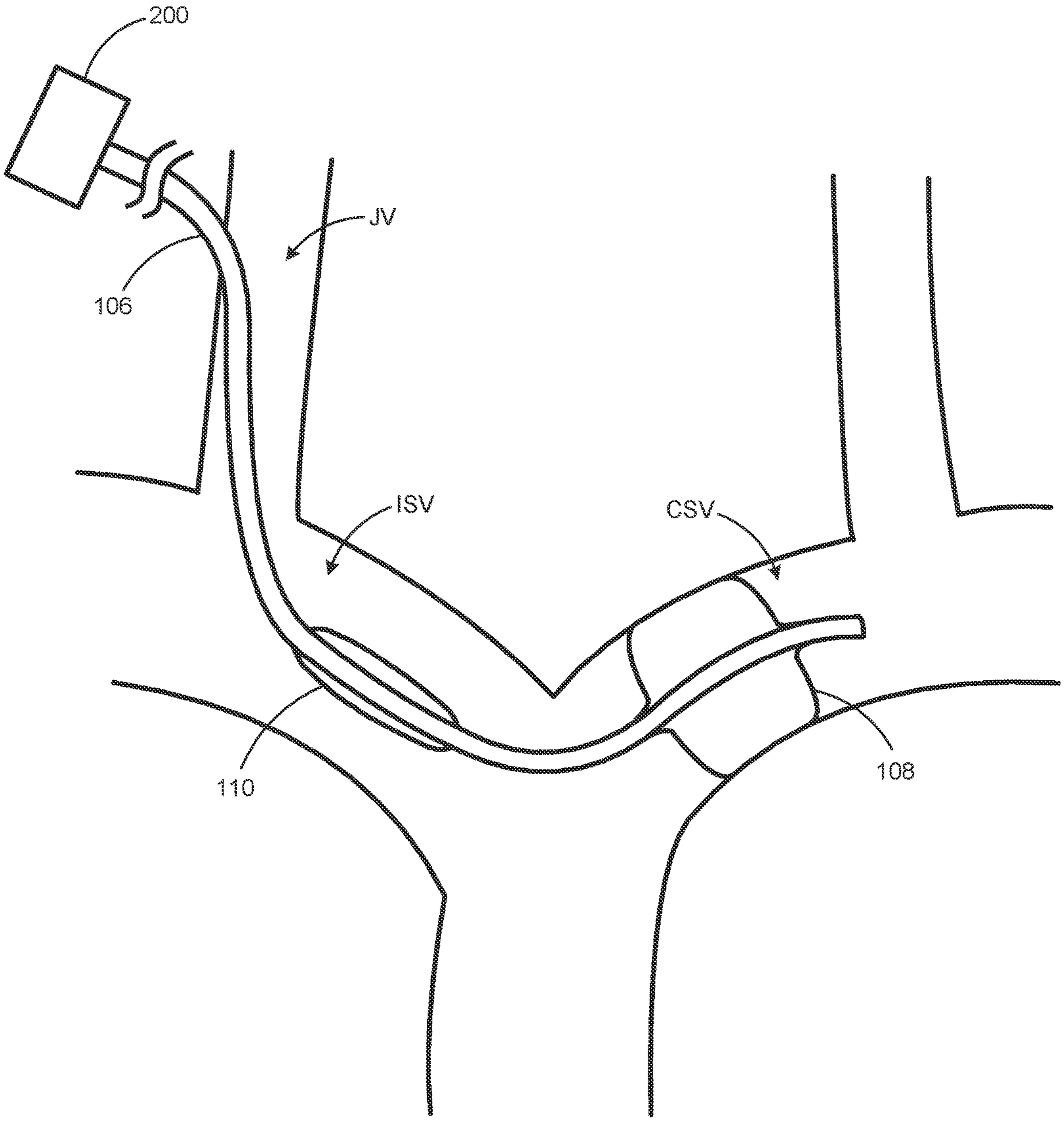
FIGS. 6A to 6D illustrate operation of the system of FIG. 1A within the contralateral and ipsilateral subclavian veins in accordance with the principles of the present disclosure.
Figure 6B:
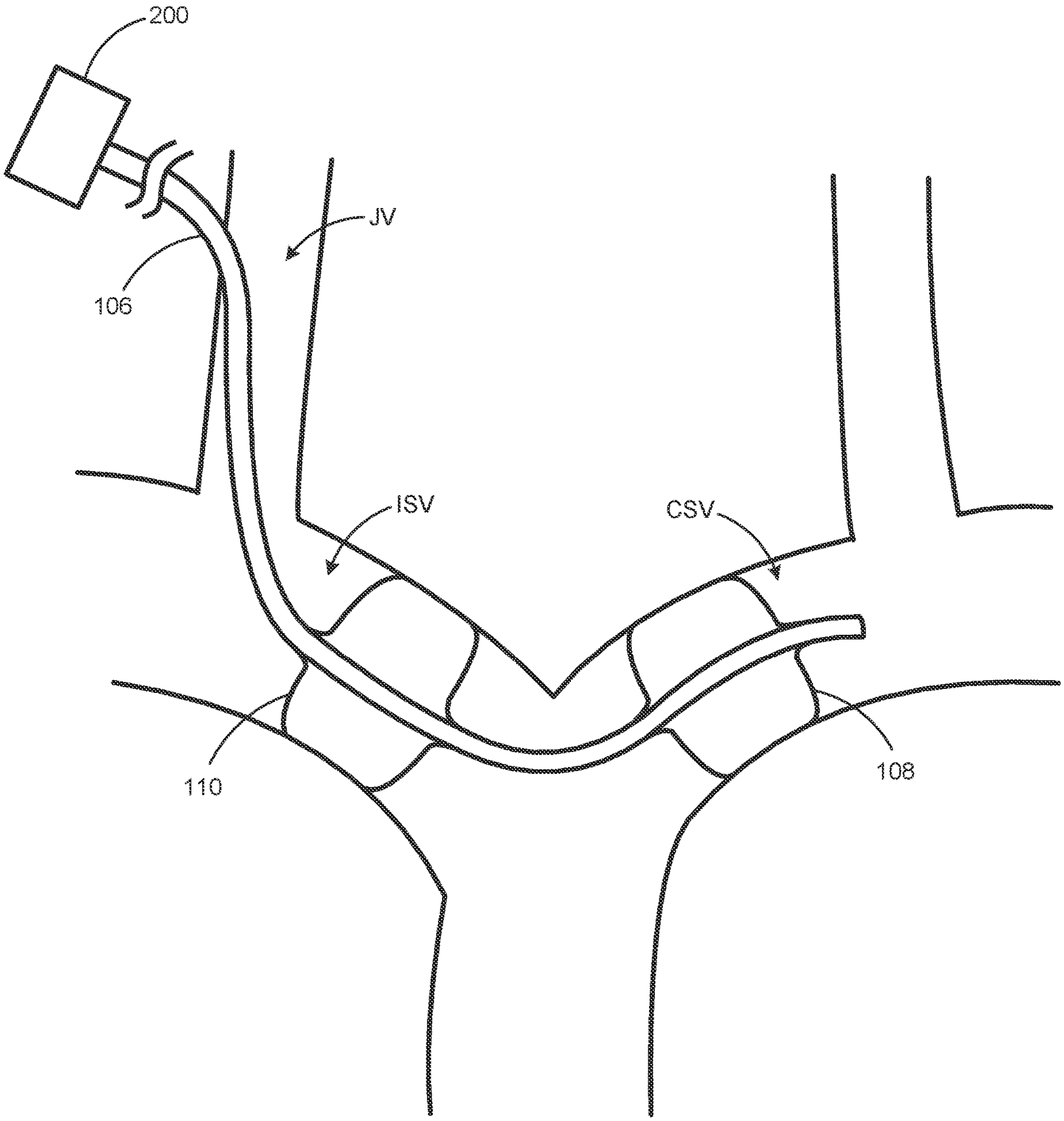
Figure 6C:
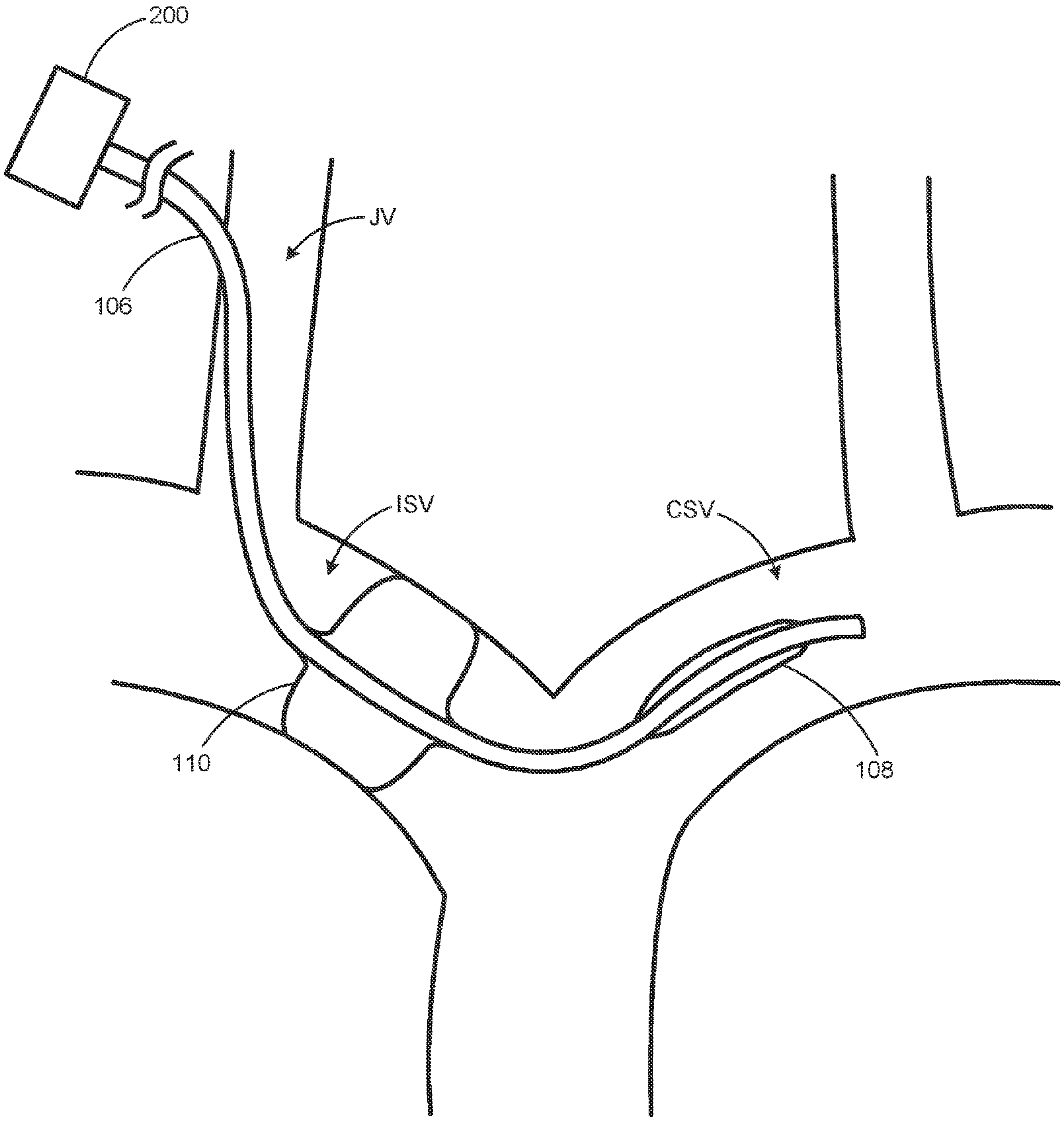
Figure 6D:
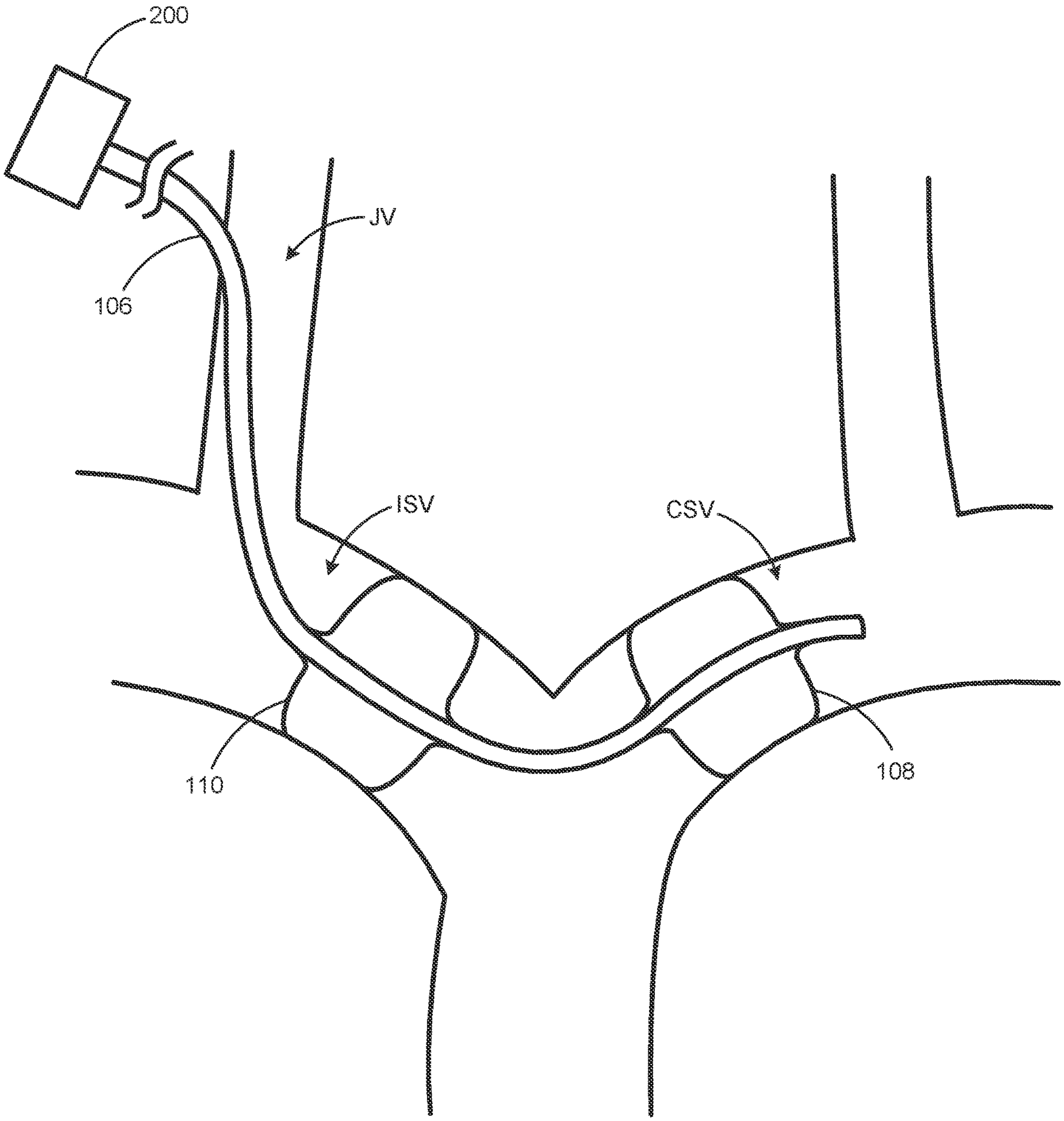

For example, for a first time period, e.g., five minutes, the predetermined actuation regimen may cause only first flow limiting element 108 to expand within the contralateral subclavian vein, as shown in FIG. 6A. For a second time period, e.g., five minutes, following the first time period, the predetermined actuation regimen may cause both first and second flow limiting elements 108, 110 to expand within the contralateral and ipsilateral subclavian veins, respectively, as shown in FIG. 6B. For a third time period, e.g., five minutes, following the second time period, the predetermined actuation regimen may cause first flow limiting element 108 to deflate, such that only second flow limiting element 110 remains expanded within the ipsilateral subclavian vein, as shown in FIG. 6C. For a fourth time period, e.g., five minutes, following the third time period, the predetermined actuation regimen may cause both first and second flow limiting elements 108, 110 to expand within the contralateral and ipsilateral subclavian veins, respectively, as shown in FIG. 6D. This actuation pattern may be repeated throughout the treatment session. Accordingly, for a fifth time period, e.g., five minutes, following the fourth time period, the predetermined actuation regimen may cause second flow limiting element 110 to deflate, such that only first flow limiting element 108 remains expanded within the contralateral subclavian vein, and so on.

Figure 7:
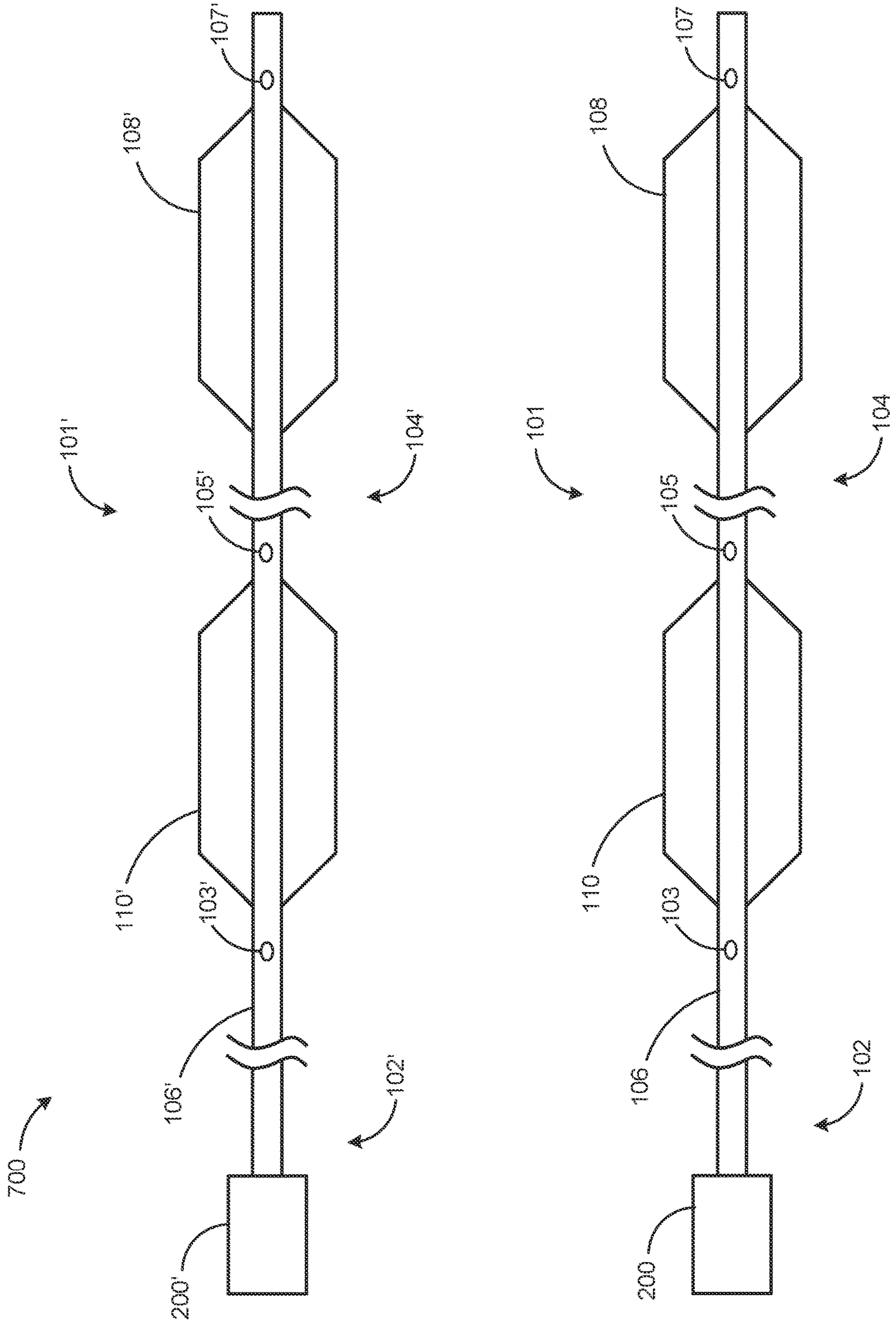
FIG. 7 illustrates another exemplary system for improving cardiac function including two dual balloon catheters constructed in accordance with the principles of the present disclosure.

Referring now to FIG. 7, exemplary system 700 for venous occlusion is provided. System 700 may be constructed similar to system 100, except that system 700 includes two balloon catheters, e.g., first balloon catheter 101 and second balloon catheter 101'. First balloon catheter 101 of system 700 may be constructed similar to the balloon catheter of system 100, and second balloon catheter 101' may be constructed similar to first balloon catheter 101, with similar components having like-prime reference numerals. However, second balloon catheter 101' differs from first balloon catheter 101 in that third and fourth flow limiting elements 108', 110' may be sized and shaped to fully occlude the contralateral and ipsilateral subclavian veins, respectively, while first and second flow limiting elements 108, 110 may be sized and shaped to fully occlude the contralateral and ipsilateral iliac veins, respectively, or vice versa.

Figure 8:
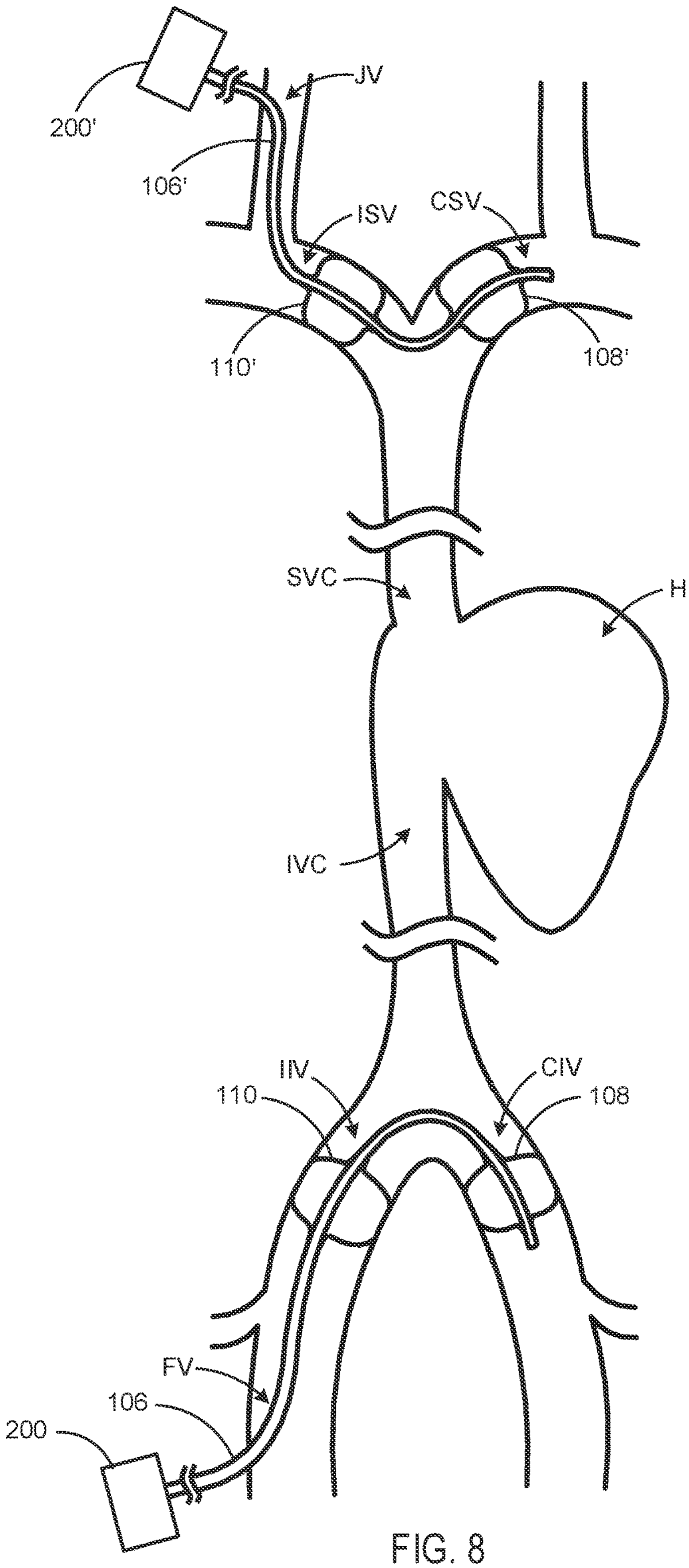
FIG. 8 illustrates the system of FIG. 7 within the contralateral and ipsilateral iliac veins and within the contralateral and ipsilateral subclavian veins in accordance with the principles of the present disclosure.

Accordingly, as shown in FIG. 8, first balloon catheter 101 may be inserted into the patient via the femoral vein using method 300 described above, such that first flow limiting element 108 is deployed within the contralateral iliac vein and second flow limiting element 110 is deployed within the ipsilateral iliac vein, and second balloon catheter 101' may be inserted into the patient via the jugular vein using method 500 described above, such that third flow limiting element 108' is deployed within the contralateral subclavian vein and fourth flow limiting element 110' is deployed within the ipsilateral subclavian vein. First and second flow limiting elements 108, 110 may be actuated via controller 200 to expand within the respective portions of the common iliac vein in accordance with the predetermined actuation regimen, to intermittently occlude the blood flow through the contralateral and ipsilateral iliac veins, and third and fourth flow limiting elements 108', 110' may be actuated via controller 200' to expand within the respective portions of the subclavian vein in accordance with the predetermined actuation regimen, to intermittently occlude the blood flow through the contralateral and ipsilateral subclavian veins, to thereby reduce cardiac preload and selectively increase arterial vascular resistance of extremities of the patient in fluid communication with the occluded veins while increasing perfusion to the patient's hearts and organs. Although two controllers are illustrated in FIGS. 7 and 8, as will be understood by a person having ordinary skill in the art, system 700 may include a single controller with a number of inflation sources corresponding with the number of flow limiting elements of system 700, such that both first and second balloon catheters 101, 101' may be coupled to the controller.

Figure 9:
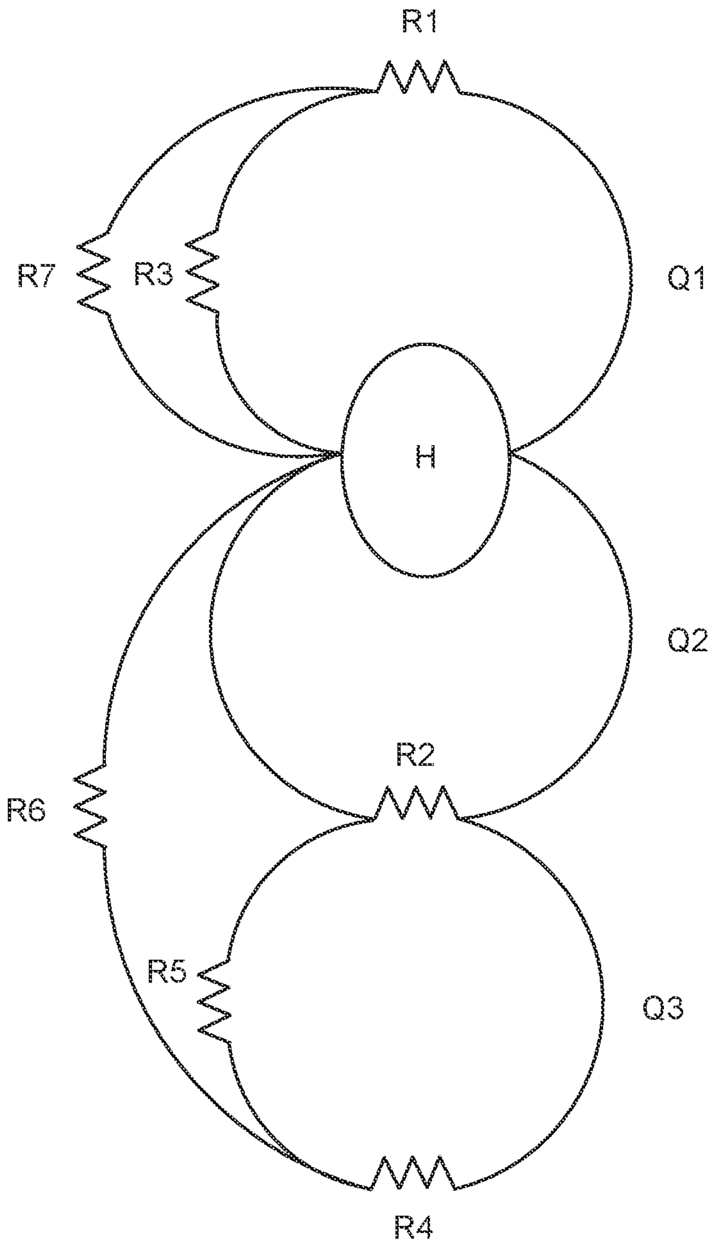
FIG. 9 is a diagram illustrating selective modulation of vascular resistance in accordance with the principles of the present disclosure.

Selective actuation of first and second balloon catheters 101, 101' provides corresponding selective occlusion of the respective veins, e.g., the common iliac vein and the subclavian vein, thereby selectively increasing vascular resistance in the respective veins, which may in turn selectively reduce arterial blood flow to the extremities in fluid communication with the occluded veins. For example, FIG. 9 is a diagram illustrating selective modulation of vascular resistance in accordance with the principles of the present disclosure. In FIG. 9, Q1 represents arterial blood flow from the heart to the patient's upper extremities, e.g., head and arms, Q2 represents arterial blood flow from the patient's lungs to the heart H and central organs, and Q3 represents arterial blood flow from the heart to the patient's lower extremities, e.g., legs. Moreover, R1 represents arterial vascular resistance to the patient's upper extremities, R2 represents arterial vascular resistance to patient's heart and central organs, and R4 represents arterial vascular resistance to the patient's lower extremities.

In addition, R3 represents venous vascular resistance as a result of occlusion of the venous vasculature in fluid communication with the patient's upper extremities, e.g., the subclavian vein, by second balloon catheter 101', and R5 represents venous vascular resistance as a result of occlusion of the venous vasculature in fluid communication with the patient's lower extremities, e.g., the common iliac vein, by first balloon catheter 101. R6 represents venous vascular resistance of collateral return of blood flow from the patient's lower extremities, and R7 represents venous vascular resistance of collateral return of blood flow from the patient's upper extremities. Accordingly, when first balloon catheter 101 is actuated to occlude the common iliac vein, e.g., via intermittent expansion of first and second flow limiting elements 108, 110, R5, and accordingly R6, increases, which causes a corresponding increase in R4, and accordingly, a corresponding decrease in Q3. Similarly, when second balloon catheter 101' is actuated to occlude the subclavian vein, e.g., via intermittent expansion of first and second flow limiting elements 108', 110', R3, and accordingly R7, increases, which causes a corresponding increase in R1, and accordingly, a corresponding decrease in Q1.

As a result, the patient's mean arterial pressure (MAP) increases, similar to the results of having the patient "clamped down" on vasopressors. However, as there is no increase in R2 (arterial vascular resistance to patient's heart and central organs), with a higher MAP, Q2 increases (i.e., perfusion to the patient's heart and organs increases) although the overall flow of the body decreases. This is because the change in Q1 and Q3 is greater than the change in Q2. Thus, the patient's heart is unloaded in a manner equivalent to the reduction in overall flow reduction of the system while keeping the patient's heart and central organs perfused. Accordingly, assuming 30% of blood flow goes to the patient's upper extremities and 20% of blood flow goes to the patient's lower extremities, the patient's heart may be unloaded by up to 50%.

Thus, system 700 may improve perfusion to the patient's heart and central organs, by selectively and intermittently occluding the venous vasculature to the patient's lower and upper extremities, e.g., increasing R5 and/or R3, which reduces arterial blood flow to the patient's lower and/or upper extremities, e.g., decreasing Q3 and/or Q1. Accordingly, arterial blood flow to the patient's extremities, e.g., lower extremities such as the legs, may be selectively reduced to maintain or improve perfusion to the patient's heart and central organs. This may be critical for a patient in a situation that requires at least minimal/adequate perfusion to the heart, and who can withstand temporarily reduced arterial blood flow to the legs, e.g., a patient that requires less oxygen to the legs. As will be understood by a person having ordinary skill in the art, selective modulation of vascular resistance may be achieved by using system 100 in either the common iliac vein in accordance with method 300 or the subclavian vein in accordance with method 500, or by using system 700 in both the common iliac vein and the subclavian vein. Moreover, in accordance with another aspect of the present disclosure, selective modulation of vascular resistance may be achieved by selectively and intermittently occluding the patient's superior vena ava (SVC) and inferior vena cava (IVC).

Figure 10:
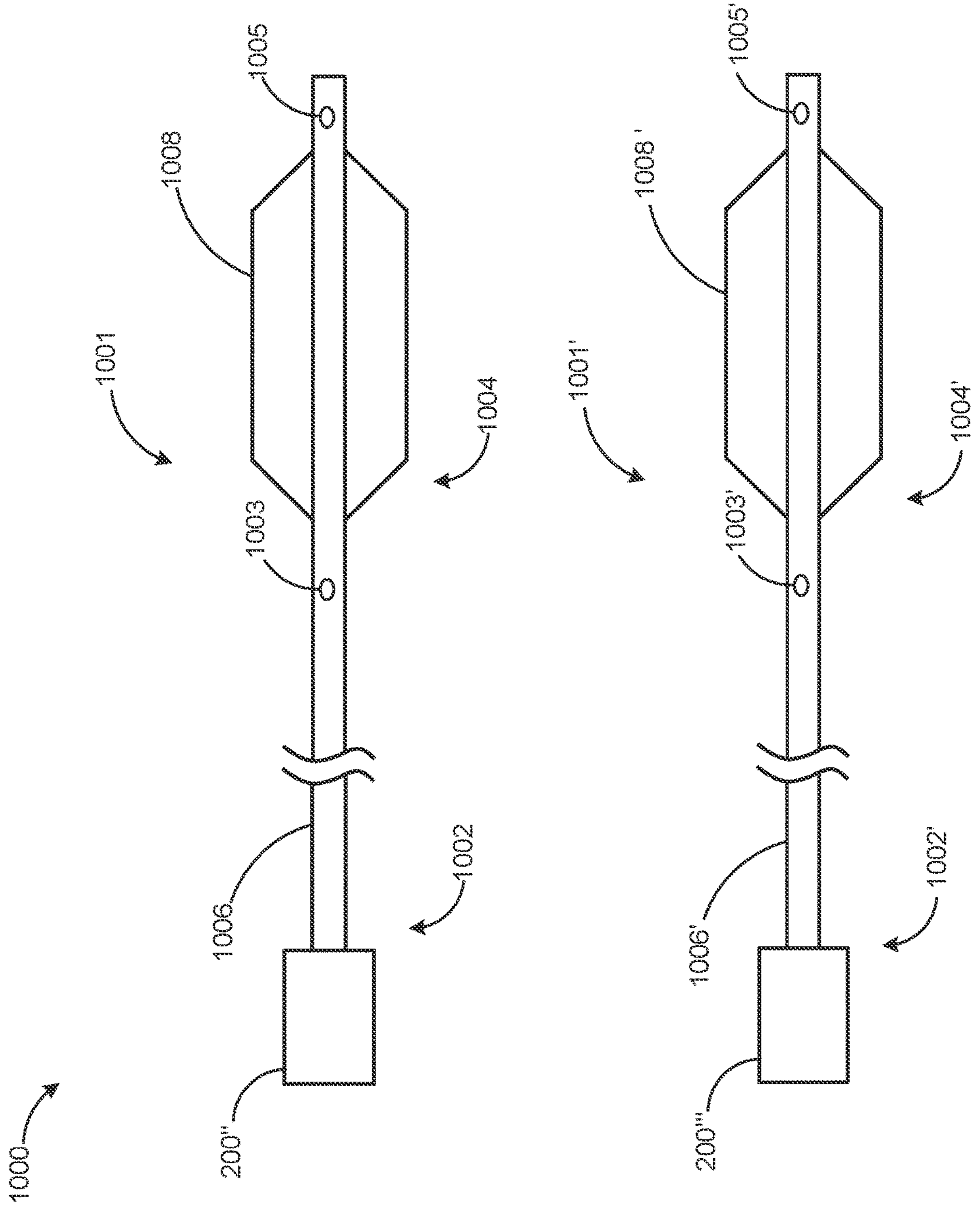
FIG. 10 illustrates another exemplary system for improving cardiac function including two balloon catheters constructed in accordance with the principles of the present disclosure.

Referring now to FIG. 10, exemplary system 1000 for venous occlusion is provided. System 1000 includes first balloon catheter 1001 and second balloon catheter 1001'. First balloon catheter 1001 includes catheter 1006 having proximal region 1002 coupled to controller 200" and distal region 1004, and an independently actuatable first flow limiting element 1008 disposed on distal region 1004. As shown in FIG. 10, first flow limiting element 1008 may be an expandable balloon that is capable of transitioning between a contracted state, allowing transluminal placement and an expanded, deployed state, to thereby selectively impede blood flow into the right atrium of the patient. First flow limiting element 1008 may be sized and shaped to fully occlude the target vein, e.g., the SVC, in the expanded state. In addition, first balloon catheter 1001 may include one or more sensors, e.g., sensor 1003 disposed on catheter 1006 proximal to first flow limiting element 1008 and sensor 1005 disposed on catheter 1006 distal to first flow limiting element 1008, for measuring one or more parameters across system 1000 and generating signals indicative of the measured parameters. Moreover, first flow limiting element 1008 is fluidicly coupled to controller 200", which may be constructed similar to controller 200, except that controller 200" may only have a single inflation source. Accordingly, controller 200" is programmed to independently and intermittently actuate first flow limiting elements 1008 in accordance to a predetermined actuation regimen stored in a memory of controller 200".

Second balloon catheter 1001' may be constructed similar to first balloon catheter 1001, with similar components having like-prime reference numerals. However, second flow limiting element 1008' of second balloon catheter 1001' may be sized and shaped to fully occlude the IVC, in the expanded state. In addition, catheter 1006' of second balloon catheter 1001' may be coupled to controller 200'", which may be constructed similar to controller 200". Accordingly, controller 200'" is programmed to independently and intermittently actuate second flow limiting elements 1008' in accordance to a predetermined actuation regimen stored in a memory of controller 200'".

Figure 11:
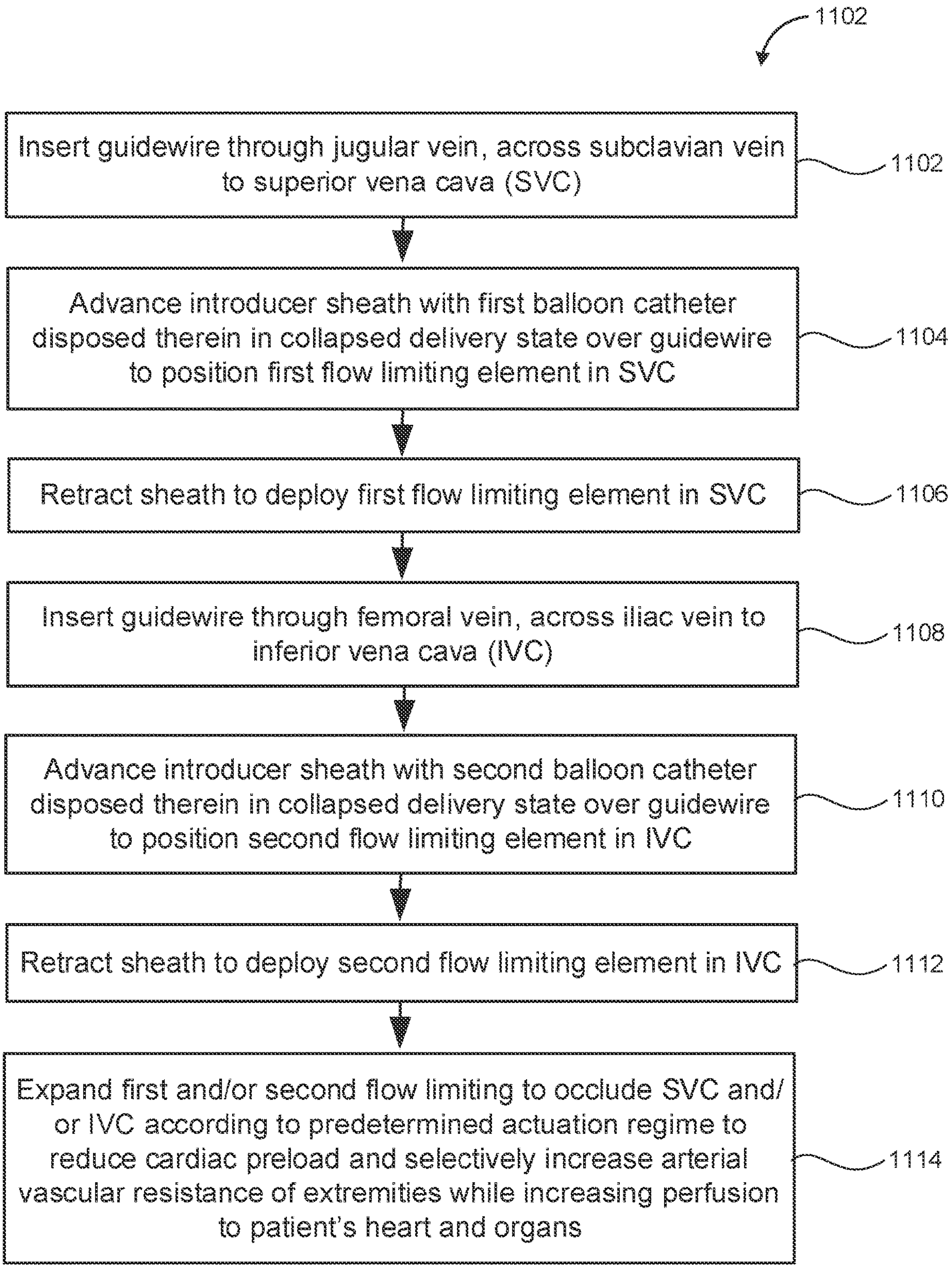
FIG. 11 is a flow chart illustrating exemplary steps for operating the system of FIG. 10 within the superior vena cava (SVC) and the inferior vena cava (IVC) to improve cardiac performance in accordance with the principles of the present disclosure.

Referring now to FIG. 11, exemplary method 1100 for delivering and operating system 1000 of FIG. 10 within the patient's SVC and IVC to improve cardiac performance is provided. Some of the steps of method 1100 may be further elaborated by referring to FIGS. 12A to 12D. At step 1102, a guidewire may be inserted into the patient through the jugular vein, down the jugular vein towards the subclavian vein, and across the subclavian vein toward the SVC. At step 1104, catheter 1006 may be inserted into an introducer sheath, such that first second flow limiting element 1008 is in its collapsed delivery state within the sheath. The introducer sheath and first balloon catheter 1001 disposed therein may then be advanced over the guidewire via a guidewire lumen of catheter 1006, until first flow limiting element 1008 is positioned within the SVC, within the sheath. The guidewire may then be removed from catheter 1006, and the guidewire lumen of catheter 1006 may be flushed prior to closing the guidewire lumen via a cap or clamp on a side-arm coupled to the guidewire lumen. The proximal end of catheter 1006 may then be coupled to controller 200", such that an inflation lumen of catheter 1006 fluidicly coupled to first flow limiting element 1008 may be coupled to an inflation source within or fluidicly coupled to controller 200". At step 1106, the sheath may be retracted relative to catheter 1006, such that first flow limiting element 1008 is deployed within the SVC.

At step 1108, a guidewire may be inserted into the patient through the femoral vein, up the femoral vein towards the common iliac vein, and across the common iliac vein toward the IVC. At step 1110, catheter 1006' may be inserted into an introducer sheath, such that second second flow limiting element 1008' is in its collapsed delivery state within the sheath. The introducer sheath and second balloon catheter 1001' disposed therein may then be advanced over the guidewire via a guidewire lumen of catheter 1006', until second flow limiting element 1008' is positioned within the IVC, within the sheath. The guidewire may then be removed from catheter 1006', and the guidewire lumen of catheter 1006' may be flushed prior to closing the guidewire lumen via a cap or clamp on a side-arm coupled to the guidewire lumen. The proximal end of catheter 1006' may then be coupled to controller 200'", such that an inflation lumen of catheter 1006' fluidicly coupled to second flow limiting element 1008' may be coupled to an inflation source within or fluidicly coupled to controller 200". At step 1112, the sheath may be retracted relative to catheter 1006', such that second flow limiting element 1008' is deployed within the IVC.

Figure 12A:
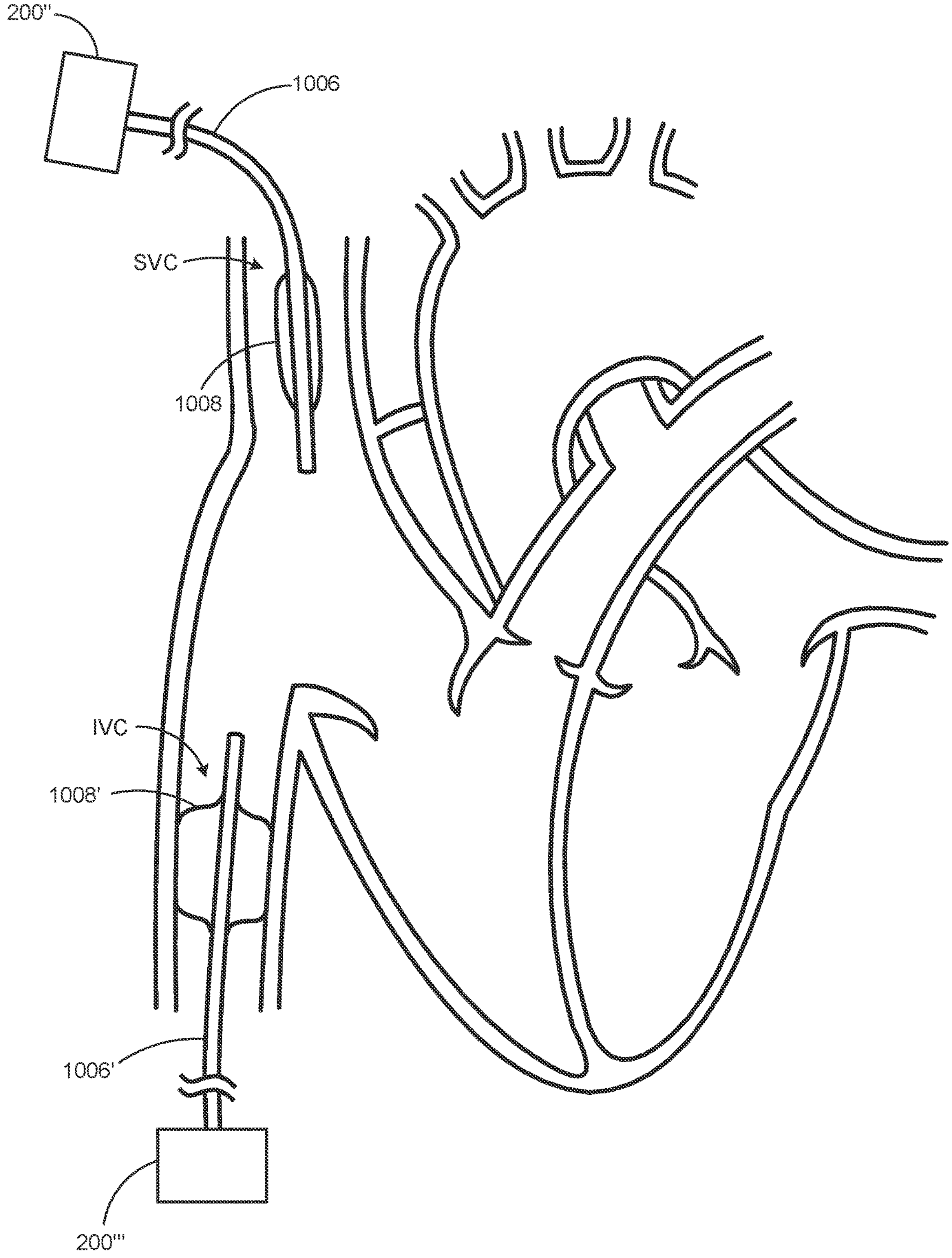
FIGS. 12A to 12D illustrate operation of the system of FIG. 10 within the SVC and the IVC in accordance with the principles of the present disclosure.
Figure 12B:
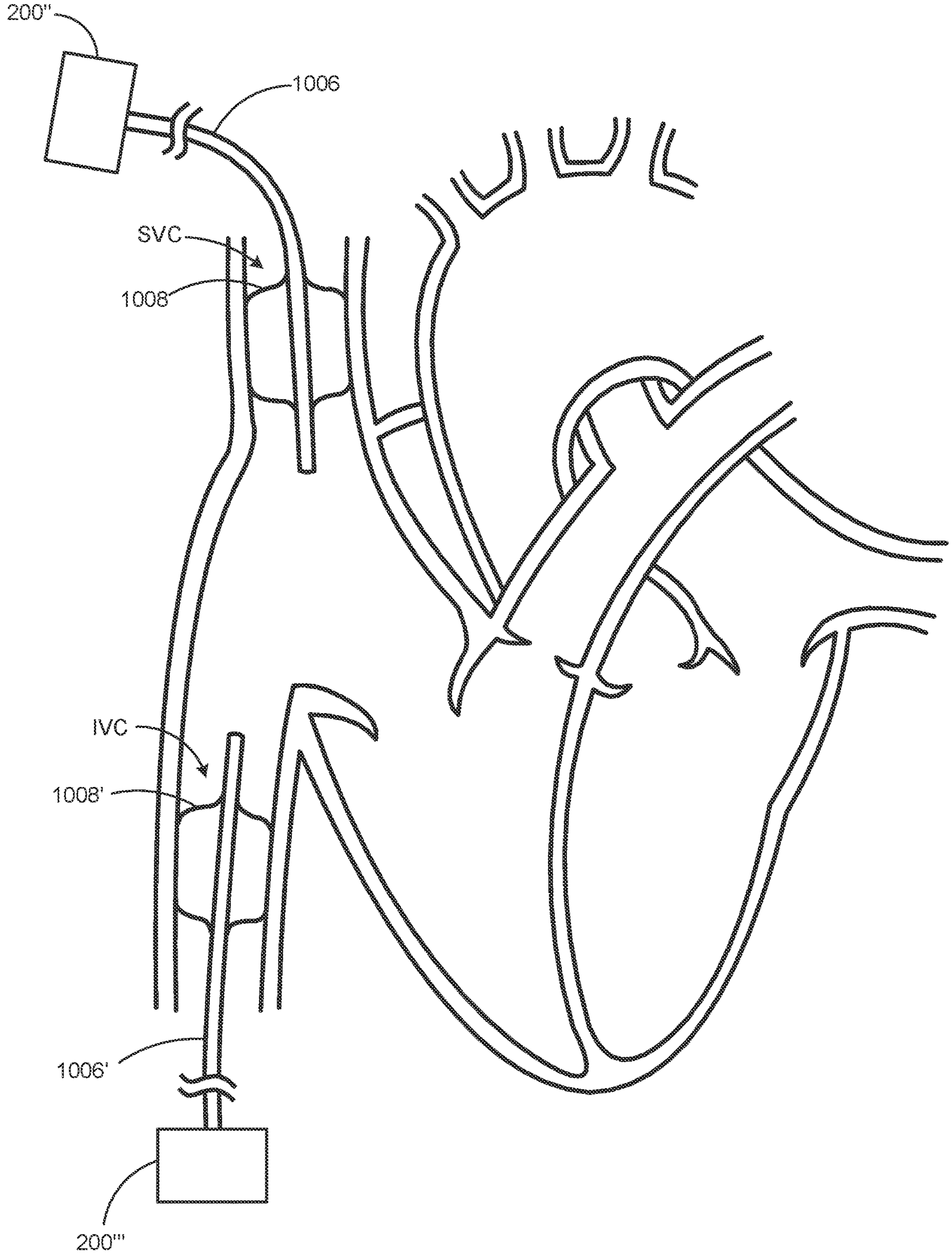
Figure 12C:
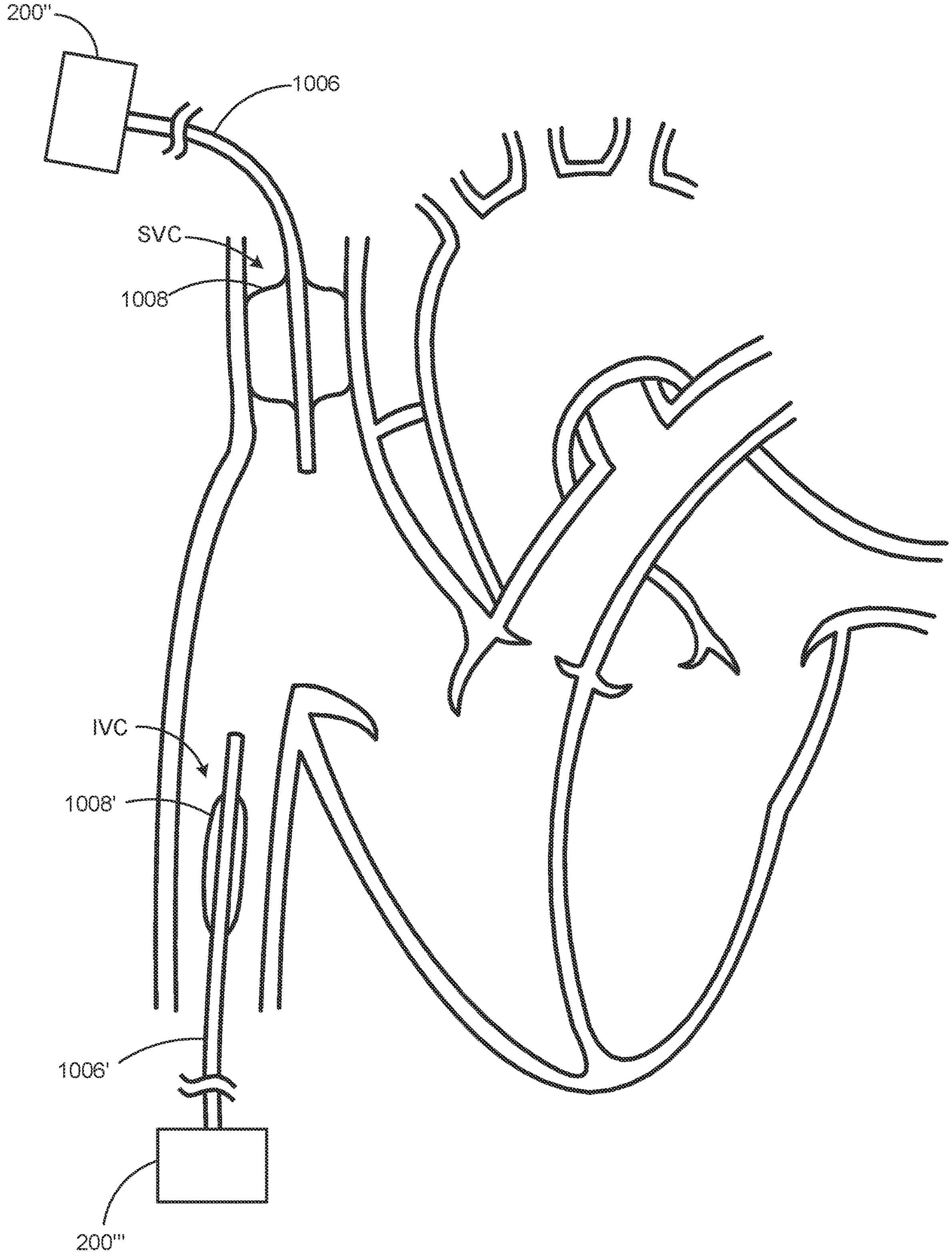
Figure 12D:
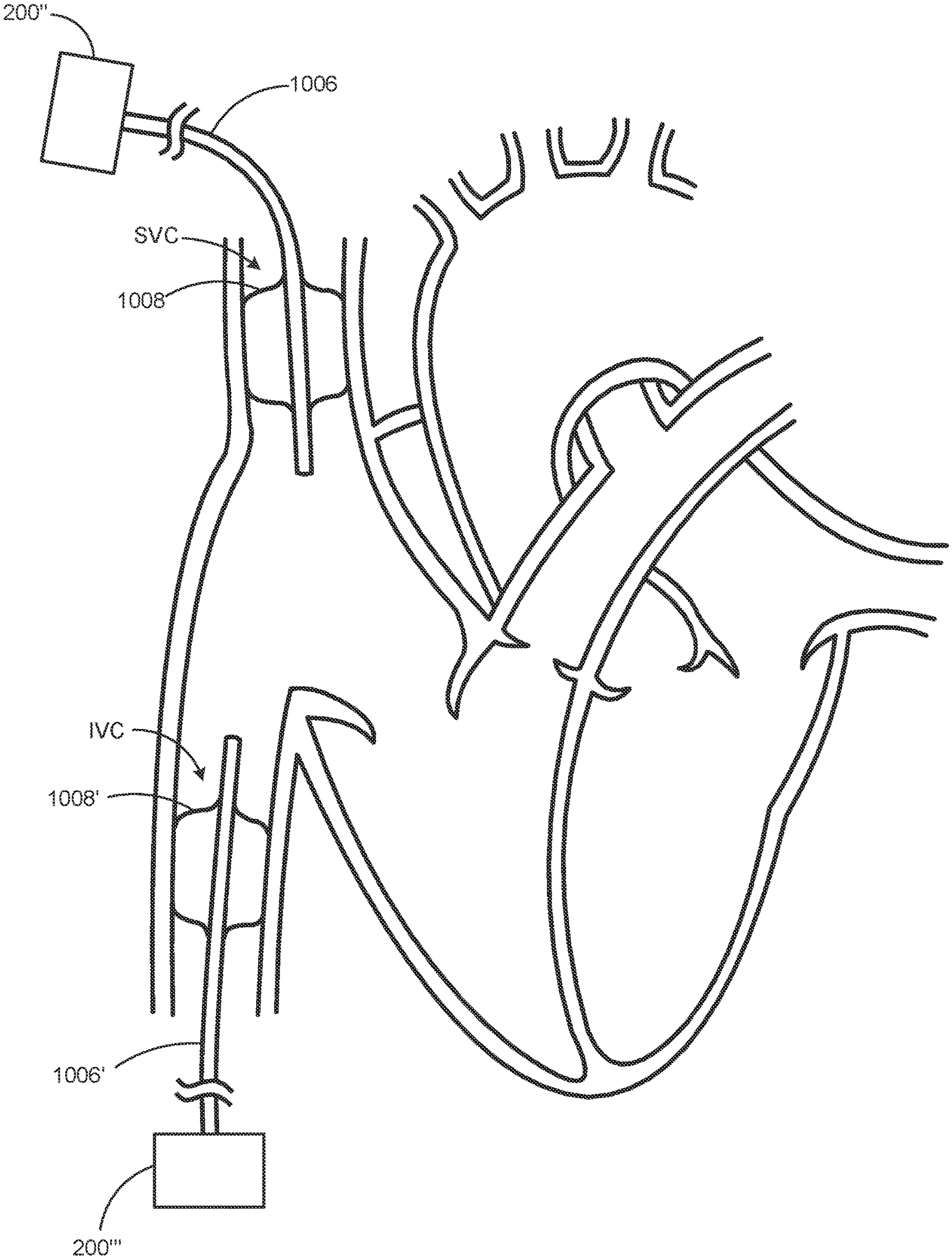

At step 1114, first and second flow limiting elements 1008, 1008' may be actuated via controllers 200", 200'", respectively, to expand within the SVC and IVC in accordance with the predetermined actuation regimen, to intermittently occlude the blood flow through the SVC and IVC to thereby reduce cardiac preload and selectively increase arterial vascular resistance of extremities of the patient in fluid communication with the occluded veins while increasing perfusion to the patient's hearts and organs. For example, for a first time period, e.g., five minutes, the predetermined actuation regimen may cause only second flow limiting element 1008' to expand within the IVC, as shown in FIG. 12A. For a second time period, e.g., five minutes, following the first time period, the predetermined actuation regimen may cause both first and second flow limiting elements 1008, 1008' to expand within the SVC and IVC, respectively, as shown in FIG. 12B. For a third time period, e.g., five minutes, following the second time period, the predetermined actuation regimen may cause second flow limiting element 1008' to deflate, such that only first flow limiting element 1008 remains expanded within the SVC, as shown in FIG. 12C. For a fourth time period, e.g., five minutes, following the third time period, the predetermined actuation regimen may cause both first and second flow limiting elements 1008, 1008' to expand within the SVC and IVC, respectively, as shown in FIG. 12D. This actuation pattern may be repeated throughout the treatment session. Accordingly, for a fifth time period, e.g., five minutes, following the fourth time period, the predetermined actuation regimen may cause first flow limiting element 1008 to deflate, such that only second flow limiting element 1008' remains expanded within the IVC, and so on.

As described above with regard to FIG. 9, selective intermittent occlusion of the SVC and IVC by system 1000 may selectively modulate vascular resistance. For example, intermittent occlusion of the SVC by first flow limiting element 1008 of system 1000 may achieve a result equivalent to intermittent occlusion of the contralateral and ipsilateral subclavian veins by third and fourth flow limiting elements 108', 110' of system 700, e.g., increased R3 and R7, and accordingly increased R1 and decreased Q1. In addition, intermittent occlusion of the IVC by second flow limiting element 1008' of system 1000 may achieve a result equivalent to intermittent occlusion of the contralateral and ipsilateral common iliac veins by first and second flow limiting elements 108, 110 of system 700, e.g., increased R5 and R6, and accordingly increased R3 and decreased Q3. Accordingly, with a higher MAP and no increase in R2, Q2 increases (i.e., perfusion to the patient's heart and organs increases) although the overall flow of the body decreases. Thus, the patient's heart is unloaded in a manner equivalent to the reduction in overall flow reduction of the system while keeping the patient's heart and central organs perfused.

Figure 13:
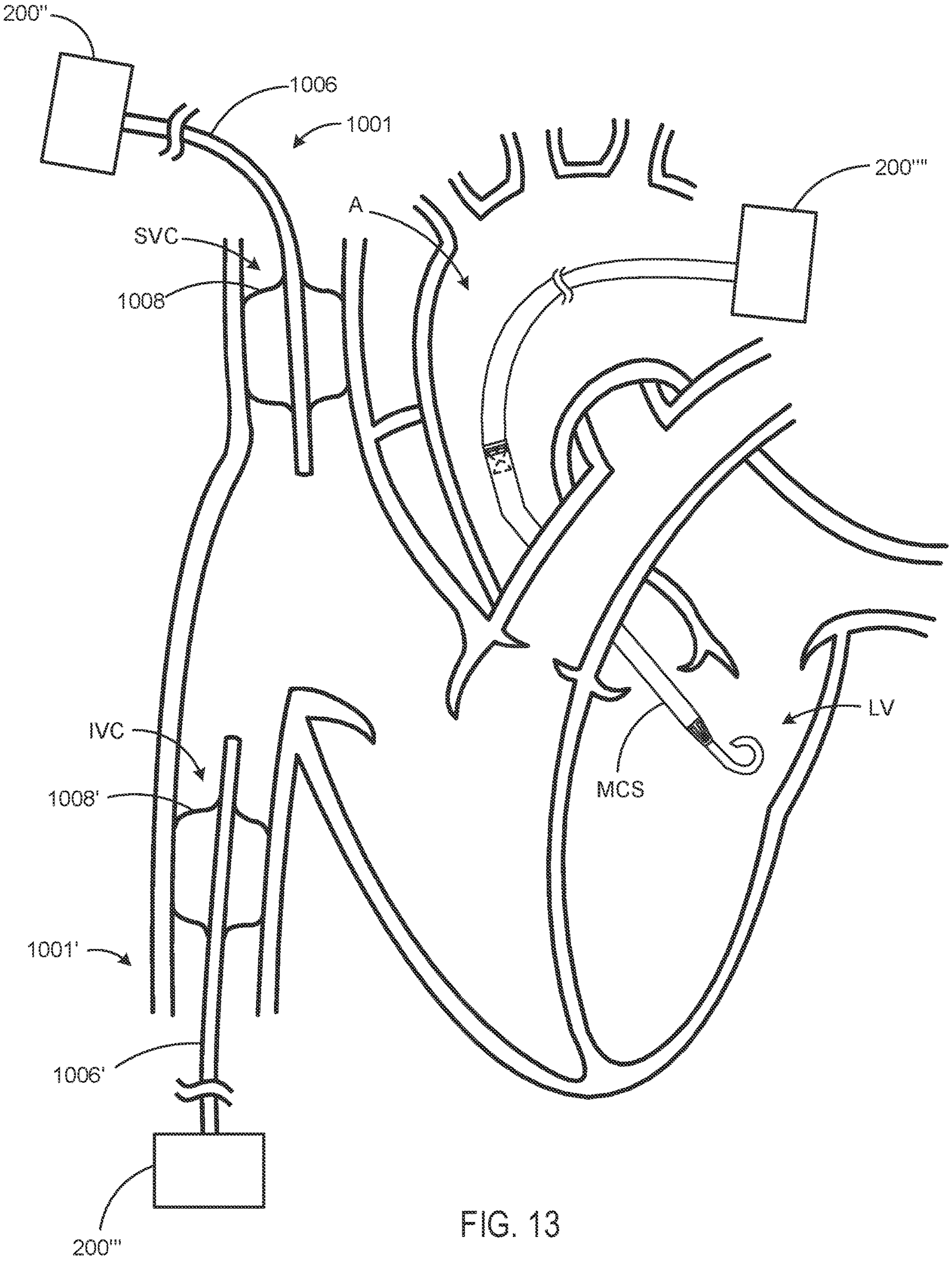
FIG. 13 illustrates additional systems for improving cardiac performance that may be used in conjunction with the systems of FIGS. 1A, 7, and 10 in accordance with the principles of the present disclosure.

Referring now to FIG. 13, additional systems for improving cardiac performance may be used in conjunction with any one of the systems of FIGS. 1A, 7, and 10 in accordance with the principles of the present disclosure. For example, as shown in FIG. 13, system 1000 having first balloon catheter 1001 positioned within the SVC and second balloon catheter 1001' positioned within the IVC, may be used in conjunction with a mechanical circulatory support (MCS) device such an Impella® heart pump (made available from Abiomed®, Danvers, Massachusetts). The MCS device includes a pump, e.g., an impeller pump, disposed on the distal region of the catheter, wherein the pump may be selectively actuated to pump blood from the left ventricle through the inflow end and expel blood into the aorta via the outflow end, and MCS device controller 200"" operatively coupled to the MCS device to actuate the pump to pump blood from the left ventricle to the aorta, thereby unloading the left ventricle and increasing coronary and systemic perfusion. MCS device controller 200"" may regulate the activation and deactivation of first flow limiting element 1008 to at least partially occlude the SVC and of second flow limiting element 1008' to at least partially occlude the IVC, simultaneously as MCS device controller 200"" actuates the pump to pump blood from the left ventricle to the aorta. Alternatively, first balloon catheter 1001 positioned within the SVC may be used in conjunction with the MCS device without second balloon catheter 1001' positioned within the IVC to improve cardiac performance. Additionally, second balloon catheter 1001' positioned within the IVC may be used in conjunction with the MCS device without first balloon catheter 1001 positioned within the SVC to improve cardiac performance. When using any of the systems described herein with an MCS device, the dimensions of the MCS may be reduced as the pump of the MCS device would be required to provide less flow to provide full unloading of the heart, thereby reducing the arterial access size. Accordingly, the dimensions of the delivery sheath also may be reduced without increasing vessel recoil to decrease insertion related to vascular complications, ischemia risk, and compatibility with small bore closure. Moreover, patients may be given vasodilators which would further increase perfusion to the heart and organs even with patients with low MAP while the vascular resistance of the arms, head, and legs would continue to be restricted.

Alternatively or additionally, system 1000 may further include an MCS device that is configured to be selectively actuated to pump blood from the SVC through an inflow end of the MCS device and expel blood into a pulmonary artery via an outflow end of the MCS device. The controller also may be operatively coupled to the MCS device to actuate the pump to pump blood from the SVC to the pulmonary artery, thereby unloading the right ventricle. For example, the controller may intermittently actuate first flow limiting element 1008 to at least partially occlude the SVC and second flow limiting element 1008' to at least partially occlude the IVC, simultaneously as the controller actuates the MCS device pump to pump blood from the SVC to the pulmonary artery.

Similarly, any one of systems 100 and 700 also may be used in conjunction with either MCS devices described above, or both, to improve cardiac performance in accordance with the principles of the present disclosure described herein. Moreover, any one of systems 100 and 700 also may be used with first balloon catheter 1001 positioned within the SVC and/or second balloon catheter 1001' disposed within the IVC to improve cardiac performance. For example, balloon catheter 101 of system 100 may be positioned within the subclavian vein, such that first flow limiting element 108 is positioned within the contralateral subclavian vein and second flow limiting element 110 is positioned within the ipsilateral subclavian vein, and first flow limiting element 1008 of second balloon catheter 1001 may be positioned within the SVC. Balloon catheter 101 and first balloon catheter 1001 may be intermittently actuated in accordance with a predetermined actuation regimen to selectively modulate vascular resistance as described above to improve cardiac performance.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A system for unloading a heart of a patient to improve cardiac performance, the system comprising:

a first flow limiting element configured to be selectively actuated to occlude a superior vena cava (SVC) in fluid communication with a first extremity of the patient;

a second flow limiting element configured to be selectively actuated to occlude an inferior vena cava (IVC) in fluid communication with a second extremity of the patient;

a controller operatively coupled to the first and second flow limiting elements, the controller configured to cause the first and/or second flow limiting elements to expand according to a predetermined actuation regimen to selectively occlude the SVC and/or IVC to reduce cardiac preload and increase mean arterial pressure to thereby selectively increase arterial vascular resistance of the patient's extremities, while maintaining arterial vascular resistance of the patient's heart and end organs and increasing perfusion to the patient's heart and end organs.

2. The system of claim 1, further comprising:

a catheter operatively coupled to the controller, wherein the first and second flow limiting elements are disposed on a distal region of the catheter.

3. The system of claim 1, wherein the predetermined actuation regimen is programmed to:

cause only the first flow limiting element to expand for a first time period;

cause the first and second flow limiting elements to expand for a second time period after the first time period;

cause only the second flow limiting element to expand for a third time period after the second time period; and cause the first and second flow limiting elements to expand for a fourth time period after the third time period.

4. The system of claim 1, wherein the predetermined actuation regimen is programmed to cause at least 70% occlusion of the SVC and IVC during a treatment period.

5. The system of claim 1, wherein the predetermined actuation regimen is programmed in the controller such that the first flow limiting element or the second flow limiting element, or both, maintains occlusion throughout a treatment session.

6. The system of claim 1, further comprising one or more sensors configured to measure one or more parameters and to generate one or more signals indicative of the one or more measured parameters.

7. The system of claim 6, wherein a first sensor of the one or more sensors is disposed proximal to the first flow limiting element and a second sensor of the one or more sensors is disposed proximal to the second flow limiting element.

8. The system of claim 6, wherein the controller is configured to adjust the predetermined actuation regimen to selectively occlude the SVC and/or IVC responsive to the one or more signals indicative of the one or more measured parameters.

9. A system for unloading a heart of a patient to improve cardiac performance, the system comprising:

a first flow limiting element configured to be selectively actuated to occlude a first vein in fluid communication with a first extremity of the patient;

a second flow limiting element configured to be selectively actuated to occlude a second vein in fluid communication with a second extremity of the patient;

a controller operatively coupled to the first and second flow limiting elements, the controller configured to cause the first and/or second flow limiting elements to expand according to a predetermined actuation regimen to selectively occlude the first and/or second veins to reduce cardiac preload and increase mean arterial pressure to thereby selectively increase arterial vascular resistance of the patient's extremities, while maintaining arterial vascular resistance of the patient's heart and end organs and increasing perfusion to the patient's heart and end organs, wherein each occlusion period during a treatment session is at least one minute.

10. The system of claim 9, wherein the first vein is a contralateral iliac vein and the second vein is an ipsilateral iliac vein.

11. The system of claim 10, further comprising a mechanical circulatory support (MCS) device.

12. The system of claim 10, further comprising:

a third flow limiting element operatively coupled to the controller, and configured to be selectively actuated to occlude a superior vena cava (SVC) of the patient, wherein the controller is configured to cause the third flow limiting element to expand according to a second predetermined actuation regimen to occlude the SVC and reduce cardiac preload.

13. The system of claim 12, further comprising a mechanical circulatory support (MCS) device.

14. The system of claim 10, further comprising:

a third flow limiting element operatively coupled to the controller, and configured to be selectively actuated to occlude a contralateral subclavian vein of the patient; and a fourth flow limiting element operatively coupled to the controller, and configured to be selectively actuated to occlude an ipsilateral subclavian vein of the patient, wherein the controller is configured to cause the third and/or fourth flow limiting elements to expand according to a second predetermined actuation regimen to selectively occlude the contralateral and/or ipsilateral subclavian veins to reduce cardiac preload and increase mean arterial pressure to thereby selectively increase arterial vascular resistance of the patient's extremities, while maintaining arterial vascular resistance of the patient's heart and end organs and increasing perfusion to the patient's heart and end organs.

15. The system of claim 14, further comprising a mechanical circulatory support (MCS) device.

16. The system of claim 14, further comprising:

a fifth flow limiting element operatively coupled to the controller, and configured to be selectively actuated to occlude a superior vena cava (SVC) of the patient, wherein the controller is configured to cause the fifth flow limiting element to expand according to a third predetermined actuation regimen to occlude the SVC and reduce cardiac preload.

17. The system of claim 16, further comprising a mechanical circulatory support (MCS) device.

18. The system of claim 9, wherein the first vein is a superior vena cava (SVC) and the second vein is an inferior vena cava (IVC).

19. The system of claim 18, further comprising a mechanical circulatory support (MCS) device.

20. The system of claim 18, further comprising:

a first catheter operatively coupled to the controller; and a second catheter operatively coupled to the controller, wherein the first flow limiting element is disposed on a distal region of the first catheter, and the second flow limiting element is disposed on a distal region of the second catheter.

21. A method for unloading a heart of a patient to improve cardiac performance, the method comprising:

positioning a first flow limiting element within a superior vena cava (SVC) in fluid communication with a first extremity of the patient;

positioning a second flow limiting element within an inferior vena cava (IVC) in fluid communication with a second extremity of the patient; and causing the first and/or second flow limiting elements to expand according to a predetermined actuation regimen to selectively occlude the SVC and/or IVC to reduce cardiac preload and increase mean arterial pressure to thereby selectively increase arterial vascular resistance of the patient's extremities, while maintaining arterial vascular resistance of the patient's heart and end organs and increasing perfusion to the patient's heart and end organs.

22. The method of claim 21, further comprising:

positioning a third flow limiting element within a contralateral iliac vein of the patient, and positioning a fourth flow limiting element within an ipsilateral iliac vein of the patient.

23. The method of claim 21, further comprising:

positioning a third flow limiting element within a contralateral subclavian vein of the patient;

positioning a fourth flow limiting element within an ipsilateral subclavian vein of the patient; and causing the third and/or fourth flow limiting elements to expand according to a second predetermined actuation regimen to selectively occlude the contralateral and/or ipsilateral subclavian veins to reduce cardiac preload and increase mean arterial pressure to thereby selectively increase arterial vascular resistance of the patient's extremities, while maintaining arterial vascular resistance of the patient's heart and end organs and increasing perfusion to the patient's heart and end organs.

24. The method of claim 21, further comprising:

positioning a third flow limiting element within a third vein of the patient; and intermittently actuating the third flow limiting element according to a second predetermined actuation regimen to occlude the third vein.

25. The method of claim 21, further comprising:

positioning a mechanical circulatory support (MCS) device within the patient's heart; and actuating the MCS device.

26. The method of claim 21, wherein causing the first and/or second flow limiting elements to expand according to the predetermined actuation regimen comprises causing the first flow limiting element or the second flow limiting element, or both, to maintain occlusion throughout a treatment session.

27. The method of claim 21, where causing the first and/or second flow limiting elements to expand according to the predetermined actuation regimen comprises:

causing only the first flow limiting element to expand for a first time period;

causing the first and second flow limiting elements to expand for a second time period after the first time period;

causing only the second flow limiting element to expand for a third time period after the second time period; and causing the first and second flow limiting elements to expand for a fourth time period after the third time period.

28. The method of claim 21, wherein each occlusion period during a treatment session is at least one minute.

* * * * *